United States Patent
Schöb et al.

[11] Patent Number: 6,053,705
[45] Date of Patent: Apr. 25, 2000

[54] ROTARY PUMP AND PROCESS TO OPERATE IT

[75] Inventors: Reto Schöb, Volketswil; Jörg Hugel, Zürich, both of Switzerland

[73] Assignees: Sulzer Electronics AG, Winterthur, Switzerland; Lust Antriebstechnik GmbH, Lahnau, Germany

[21] Appl. No.: 09/066,435

[22] PCT Filed: Sep. 26, 1996

[86] PCT No.: PCT/CH96/00335

§ 371 Date: May 6, 1998

§ 102(e) Date: May 6, 1998

[87] PCT Pub. No.: WO98/11650

PCT Pub. Date: Mar. 19, 1998

[30] Foreign Application Priority Data

Sep. 10, 1996 [WO] WIPO ............... PCT/CH96/00310

[51] Int. Cl.$^7$ .................................................. F04B 35/04
[52] U.S. Cl. .................... 417/53; 417/356; 417/423.12
[58] Field of Search ....................... 417/53, 356, 423.12

[56] References Cited

U.S. PATENT DOCUMENTS

| | | |
|---|---|---|
| 4,779,614 | 10/1988 | Moise . |
| 5,112,200 | 5/1992 | Isaacson . |
| 5,385,581 | 1/1995 | Bramm . |
| 5,470,208 | 11/1995 | Kletschka . |
| 5,484,266 | 1/1996 | Murga . |
| 5,507,629 | 4/1996 | Jarvik ...................................... 417/356 |

FOREIGN PATENT DOCUMENTS

| | | |
|---|---|---|
| 0467234 A2 | 1/1992 | European Pat. Off. . |
| 2 681 384 | 3/1993 | France . |
| 2406790 | 8/1975 | Germany . |

OTHER PUBLICATIONS

Bramm, G., et al. "Axial Centrifugal Blood Pump with Magnetically Suspended Rotor", in: *Proc. ESAO* (1982) Sep. 1–3, Brussels, Belgium.

Primary Examiner—Ronald Capossela
Attorney, Agent, or Firm—Townsend and Townsend and Crew LLP

[57] ABSTRACT

The rotary pump (3) according to the invention comprises a housing (9) and a rotor (2) with blades (1b) located inside the housing (9), with the rotor (2) comprising a passive, magnetically effective rotor part (1) and the housing (9) being surrounded by a stator (7) that has electrical windings (8a, 8b, 8c, 8d, 8e, 8f, 8g, 8h) and teeth (7a, 7b, 7c, 7d, 7e, 7f, 7g, and 7h), with the stator (7) and the rotor part (1) forming a bearingless motor, and with the rotor part (1) being actively controllable and drivable by means of the electrical windings (8a, 8b, 8c, 8d, 8e, 8f, 8g, 8h) relative to three degrees of freedom, and with the rotor part (1) and the teeth (7a, 7b, 7c, 7d, 7e, 7f, 7g, and 7h) of the stator (7) being designed to be geometrically adapted to one another and arranged with respect to one another in such fashion that the rotor part (1) can be held by passively acting reluctance forces in the stator (7) with respect to three additional non-actively-controllable degrees of freedom, in order to locate the rotor (2) inside the housing (9) in a drivable and floating fashion with zero contact.

19 Claims, 21 Drawing Sheets

Fig. 2a  Fig. 2b    Fig. 2e  Fig. 2f
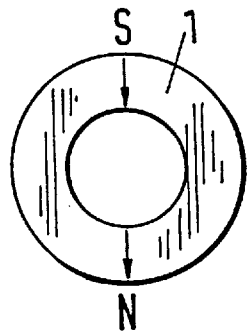     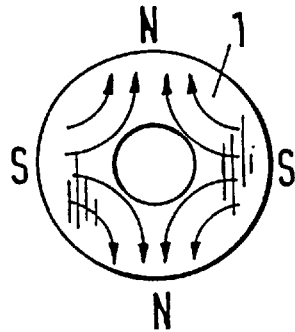 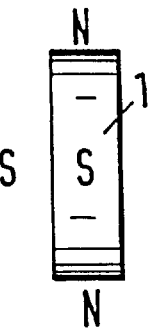
Fig. 2c  Fig. 2d    Fig. 2g  Fig. 2h
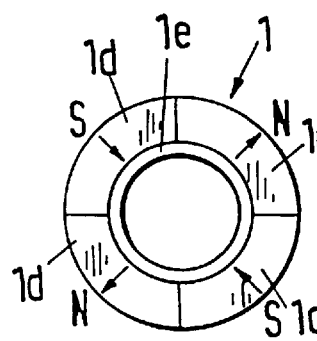 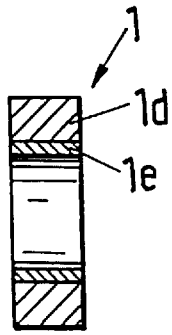    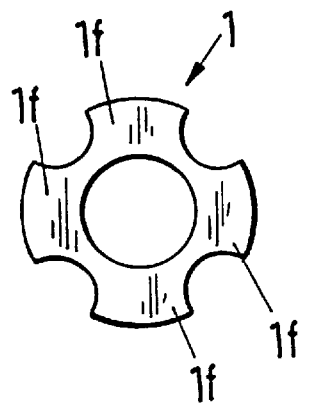 

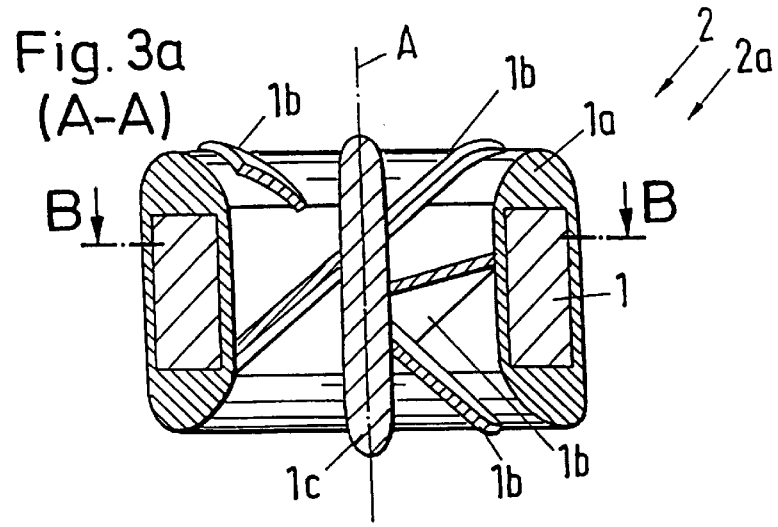
Fig. 3a (A-A)
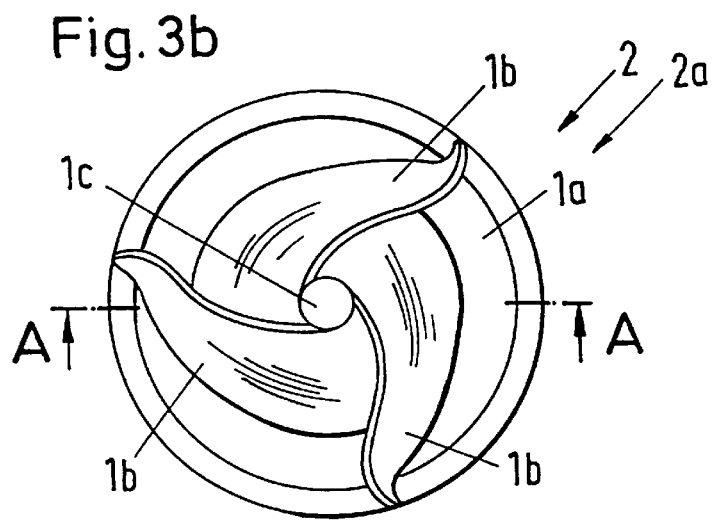
Fig. 3b
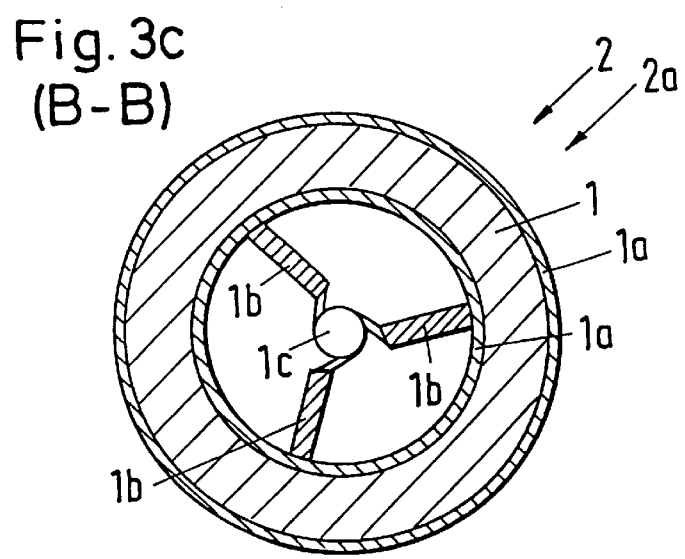
Fig. 3c (B-B)

$N_{17} = 0$
$N_{27} = 200$
$N_{37} = 200$
$N_{47} = 0$ $N_{16} = 141$
$N_{26} = 141$
$N_{36} = 0$
$N_{46} = 200$ $N_{18} = 141$
$N_{28} = 141$
$N_{38} = 0$
$N_{48} = 200$ $N_{15} = 200$
$N_{25} = 0$
$N_{35} = 200$
$N_{45} = 0$ $N_{11} = 200$
$N_{21} = 0$
$N_{31} = 200$
$N_{41} = 0$

W1 : $N_{14} = 141$
W2 : $N_{24} = 141$
W3 : $N_{34} = 0$
W4 : $N_{44} = 200$ $N_{12} = 141$
$N_{22} = 141$
$N_{32} = 0$
$N_{42} = 200$ $N_{13} = 0$
$N_{23} = 200$
$N_{33} = 200$
$N_{43} = 0$

|  | Antriebs-wicklung | Steuer-wicklung |
|---|---|---|
|  | $P_1=1, m=2$ | $P_1=2, m=2$ |
| Phase 1 | --- W1 | --..-- W3 |
| Phase 2 | ___ W2 | ___ W4 |

(D-D)

(C-C)

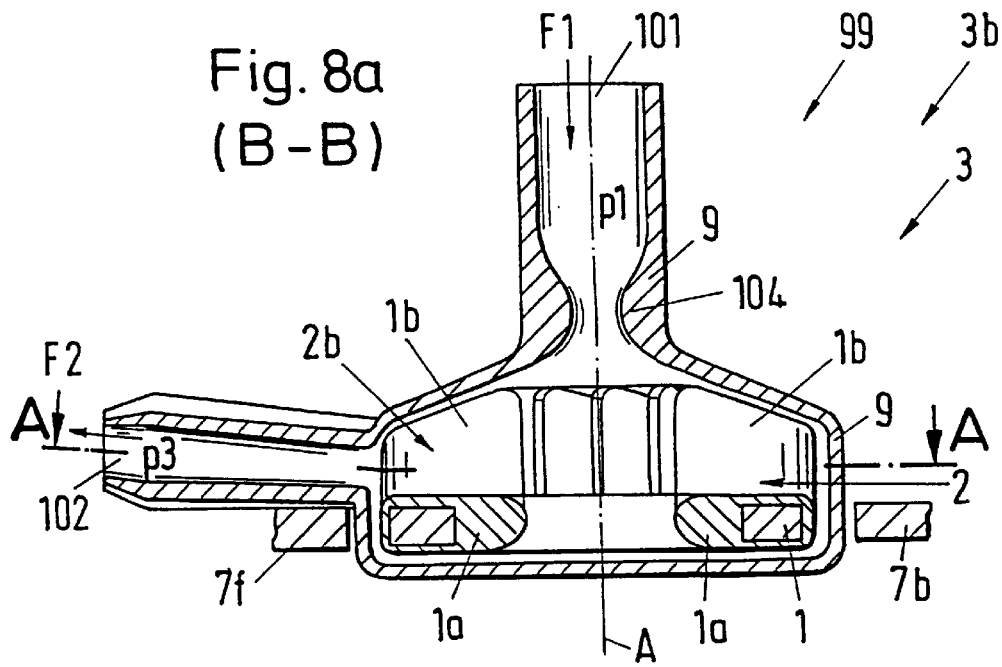
Fig. 8a (B-B)
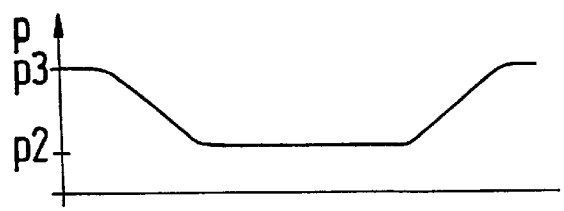
Fig. 8i
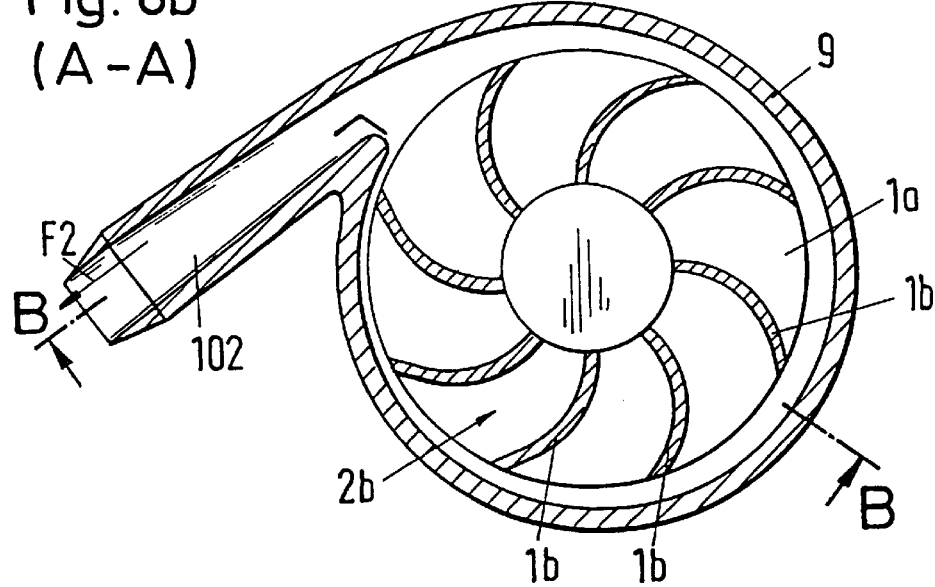
Fig. 8b (A-A)

(C-C)

(D-D)

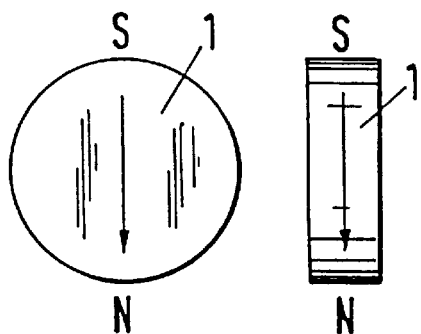
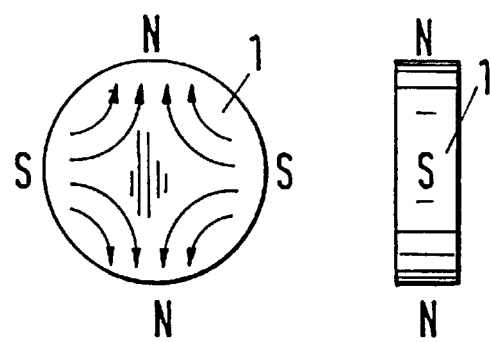
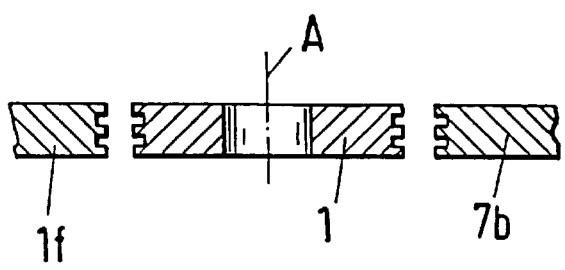
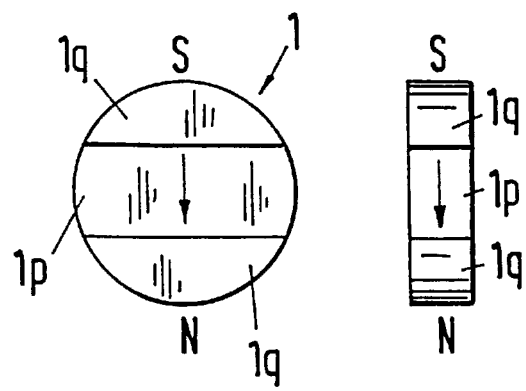

ROTARY PUMP AND PROCESS TO OPERATE IT

The invention relates to a rotary pump according to the preamble of claim 1 as well as to a method for operation thereof according to the preamble of claim 22.

Known rotary pumps, for example axial pumps or centrifugal pumps have a rotor that is rotatably mounted in mechanical bearing devices. Rotary pumps of this type suffer from the disadvantage that the delivered fluid is contaminated by lubricants or mechanical abrasion of the bearing devices or of the rotor, so that such pumps are not suitable for delivering fluids that must not be contaminated. Fluids of this kind include for example super-pure water or blood. In addition, such rotary pumps are not suitable for delivering aggressive fluids, since the bearing devices would be destroyed in a short time.

The goal of the present invention is to propose an economically more advantageous rotary pump.

This goal is achieved by a rotary pump having a bearingless motor. The rotary pump includes a housing defining an inlet, an outlet, and a passage extending between the inlet and the outlet for enabling a fluid to be pumped from the inlet to the outlet. A stator is arranged to extend around the housing defining the passage. This stator has a plurality of magnetically conducting stator teeth wound with electrical windings. A rotor with fluid impelling blades is contained inside the housing at the passage for rotating around an axis within the passage. This rotation causes fluid to be pumped from the inlet to the outlet of the housing. A passive magnetically effective rotor part is comprised by the rotor. An electrical control is provided to the electrical windings to generate a rotating magnetic field for causing rotation of the rotor. This same electrical control controls the magnetic field to position the passive magnetically effective rotor part relative to the stator in a plane normal to the axis. At the same time, the passive magnetically effective rotor part has a passive magnetic attraction to the magnetically conducting teeth of the stator to resist rotor displacement along the axis and to resist tilting of the rotor relative to a plane normal to the axis. The electrical driving of the pump can be inductive, reluctance or synchronous. Further, the following discloses a process for the control of a rotary pump. For example, the pump has a use in the pumping of blood, either inside or outside the human body.

The goal is achieved by a rotary pump with a rotor that is mounted and drivable with zero contact by magnetically acting forces inside a housing of the rotary pump. One advantage of the invention consists in the fact that the housing permits hermetic separation between the electromagnets that are controllable and are located outside the housing and the fluid flowing inside the housing. There are no openings whatever in the housing. In addition, the rotor is mounted with zero contact inside the housing, so that no lubricants are required and there is no abrasion by bearing devices.

The invention is achieved in particular by a rotary pump comprising a housing and an impeller with a rotational axis located inside the housing, with the impeller having a passive magnetically effective rotor part and the housing being surrounded by a stator that has electrical coils and teeth, said coils and teeth being arranged, designed, and controllable in such fashion that the stator and the rotor part cooperate as a bearingless motor.

The use of a bearingless motor makes the rotor part actively controllable in three degrees of freedom and allows the position of the rotor part to be defined in a plane running perpendicularly to the rotation axis in the x and y directions and a torque that acts in the circumferential direction on the rotor part can also be predetermined by a corresponding control of the electrical coils.

In an especially advantageous embodiment of the invention, the rotor part and the teeth of the stator are designed with geometric mutual adaptation and arranged relative to one another in such fashion that the rotor part can be held by passively acting reluctance forces in the stator relative to three additional non-actively-controllable degrees of freedom in order to locate the rotor within the housing so that it floats, can be driven, and is stable with zero contact. One advantage of this arrangement lies in the fact that the position of the rotor relative to a plane that runs perpendicularly to the rotation axis is actively controllable, that a controllable torque can act on the rotor, and that the position of the rotor relative to the additional three degrees of freedom is maintained in a stable position in the stator by passively acting magnetic forces.

The rotary pump according to the invention is preferably designed as an axial pump or a centrifugal pump, with the rotor accordingly being designed as an axial impeller of an axial pump or as a centrifugal impeller of a centrifugal pump.

The rotor, designed as an axial impeller, produces a thrust acting in the axial direction on the fluid delivered. The rotor, designed as a centrifugal impeller, likewise experiences a force acting in the axial direction during pump operation. The magnetically effective rotor part, a component of the axial impeller or of the centrifugal impeller, is held in the direction of the rotation axis or in the axial direction only by passively acting magnetic forces.

The stator and rotor part therefore are so designed that a passively acting magnetic force that is sufficiently high to operate the rotary pump acts on the rotor. This can be accomplished by a suitable design and geometric arrangement of the magnetically effective components of the rotor part and stator part, with the teeth of the stator part for example having approximately the same height in the axial direction as those of the rotor part and the diameter of the rotor part being made at least twice as large as its height in the axial direction. The passively acting magnetic force in the axial direction can also be increased by permanent magnetic pretensioning of the stator as well as of the rotor part. The bearing force in the axial direction can also be increased by additional bearing devices such as a hydrodynamically acting bearing. In addition, it may prove to be advantageous to provide a mechanical bearing device that acts in the axial direction, said device, at very high axial forces, serving as an emergency bearing device to hold the rotor part in a specific position.

The term "bearingless motor" refers to an electrically controllable bearing and drive device that comprises a rotor as well as a stator that has electromagnetic coils. The rotor of the bearingless motor is drivable in accordance with principles of electrical machines that are known of themselves, thus in accordance with the operating principles of a synchronous motor, a reluctance motor, or an induction motor. The rotor of the bearingless motor is held in the stator with zero contact in a plane perpendicular to the rotation axis by magnetically acting forces. The electromagnetic coils can be controlled in such fashion that the position of the rotor in a plane that runs perpendicularly to the rotation axis of the rotor can be actively influenced. The position of the rotor is monitored by sensors and the electromagnetic coils are controlled adjustably by a suitably designed control device in such fashion that the rotor is held with zero contact in the stator relative to the plane that runs perpendicularly to the rotation axis of the rotor. In addition, by suitable control exerted on the electromagnetic coils of the stator, a torque can be created to act on the rotor so that the rotor undergoes rotation around its axial axis. A so-called bearingless motor of this kind can therefore actively control a rotor relative to three degrees of freedom, namely its positions in the x and y directions as well as rotation around its axis. A bearingless motor having these properties can be designed by using a variety of construction methods.

A bearingless motor can be designed for example as a reluctance motor, in which the rotor is made cruciform for example and the stator is composed of a plurality of coils that can be individually controlled electrically, said coils extending in the radial direction and being mounted in the circumferential direction around the rotor. These coils can be controlled in such fashion that the rotor is suspended relative to a plane that is perpendicular to the rotation axis and the rotor can also be drivable to rotate around its rotation axis, with a magnetic rotary field being generated by the coils.

A bearingless motor can be designed for example to be similar to a synchronous motor, with the rotor having a permanent magnet extending in the radial direction and the stator having a rotary field winding, also known as a drive winding, to generate a rotary field, said field driving the rotor so that it rotates around its rotation axis. In addition the stator has a control winding to control the position of the rotor in a plane that extends perpendicularly to the rotation axis, with the position of the rotor or the magnetic flux being detected by sensors and with the control winding being controlled by a control device in such fashion that the rotor is held in the stator with zero contact in the plane that extends perpendicularly to the axis of the stator. In one embodiment, a so-called bearingless motor of this design has a drive winding with a pole pair number p and a control winding with a pole pair number p+1 or p−1.

The rotary pump according to the invention, designed as an axial pump or a centrifugal pump, is especially suitable for delivering highly purified aggressive or explosive toxic fluids and liquids. The rotary pump according to the invention is likewise suitable as a blood pump operated outside or inside the human body.

One advantage of the rotary pump according to the invention consists in the fact that because of its zero contact mounting, the rotor can be operated at a very high rpm so that the rotary pump has a high delivery capacity even in very small sizes. A further advantage of the rotary pump according to the invention consists in the fact that the rotor can also be operated at an rpm that varies over time and the fluid can also be delivered in pulses. The rpm of the rotor is freely controllable between a stopped position and a very high rpm, so that the rotary pump exhibits high dynamics relative to the quantity delivered, and very small as well as very large quantities of fluid can be delivered, with the fluid being deliverable in particular in pulses, as a predetermined quantity of fluid per unit time.

The invention will now be described in detail with reference to a plurality of embodiments.

Figure 1:
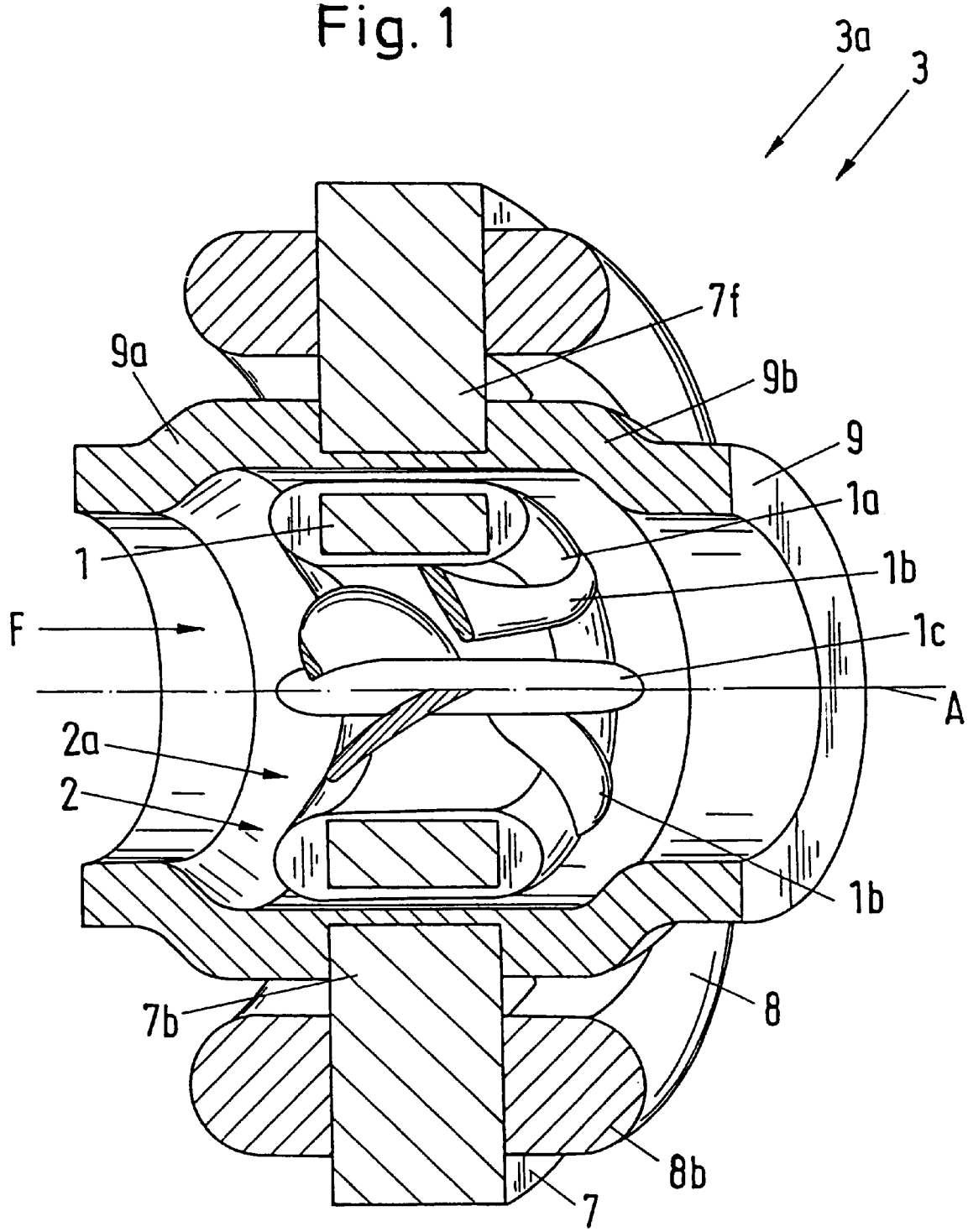
FIG. 1 is a lengthwise section through an axial pump.
Figure 1A:
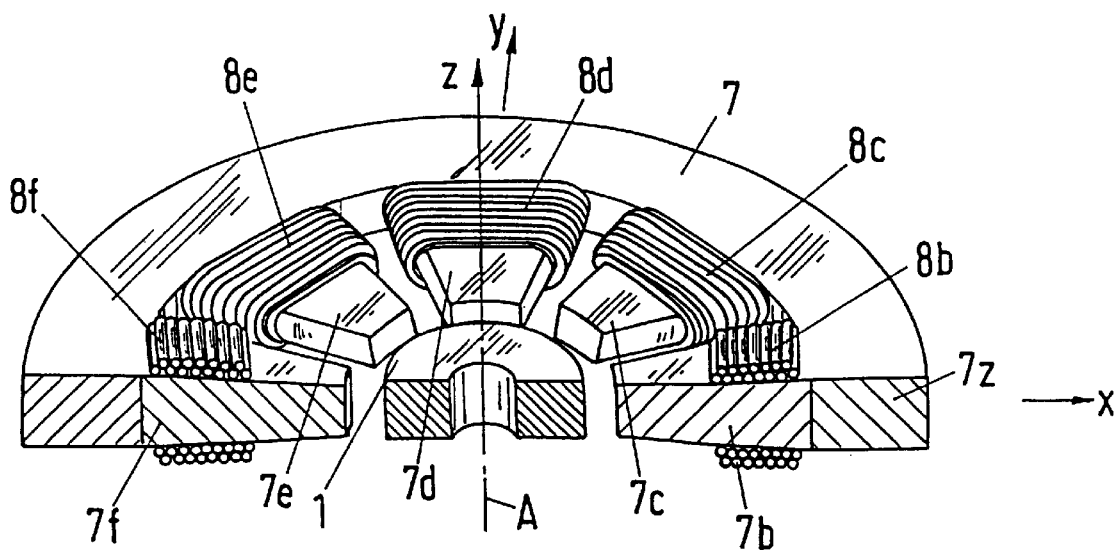
FIG. 1a is a section through a stator and a magnetically effective rotor part of the axial or centrifugal pump.
Figure 1B:
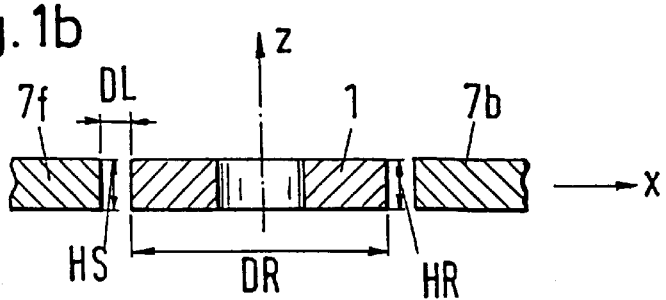
Figure 1C:
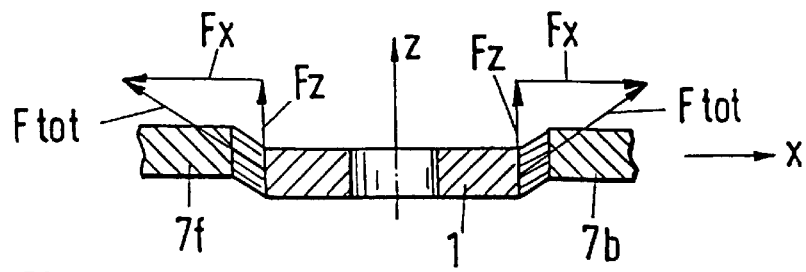
Figure 1D:
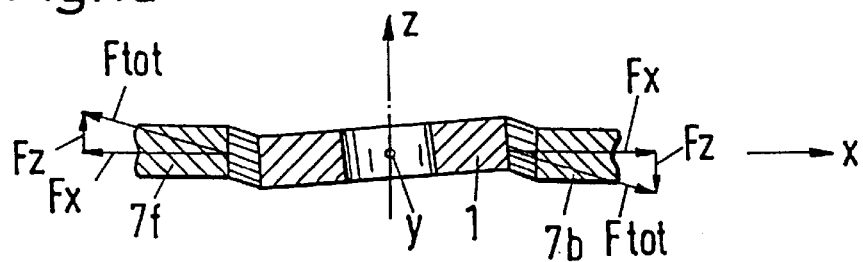
Figure 4A:
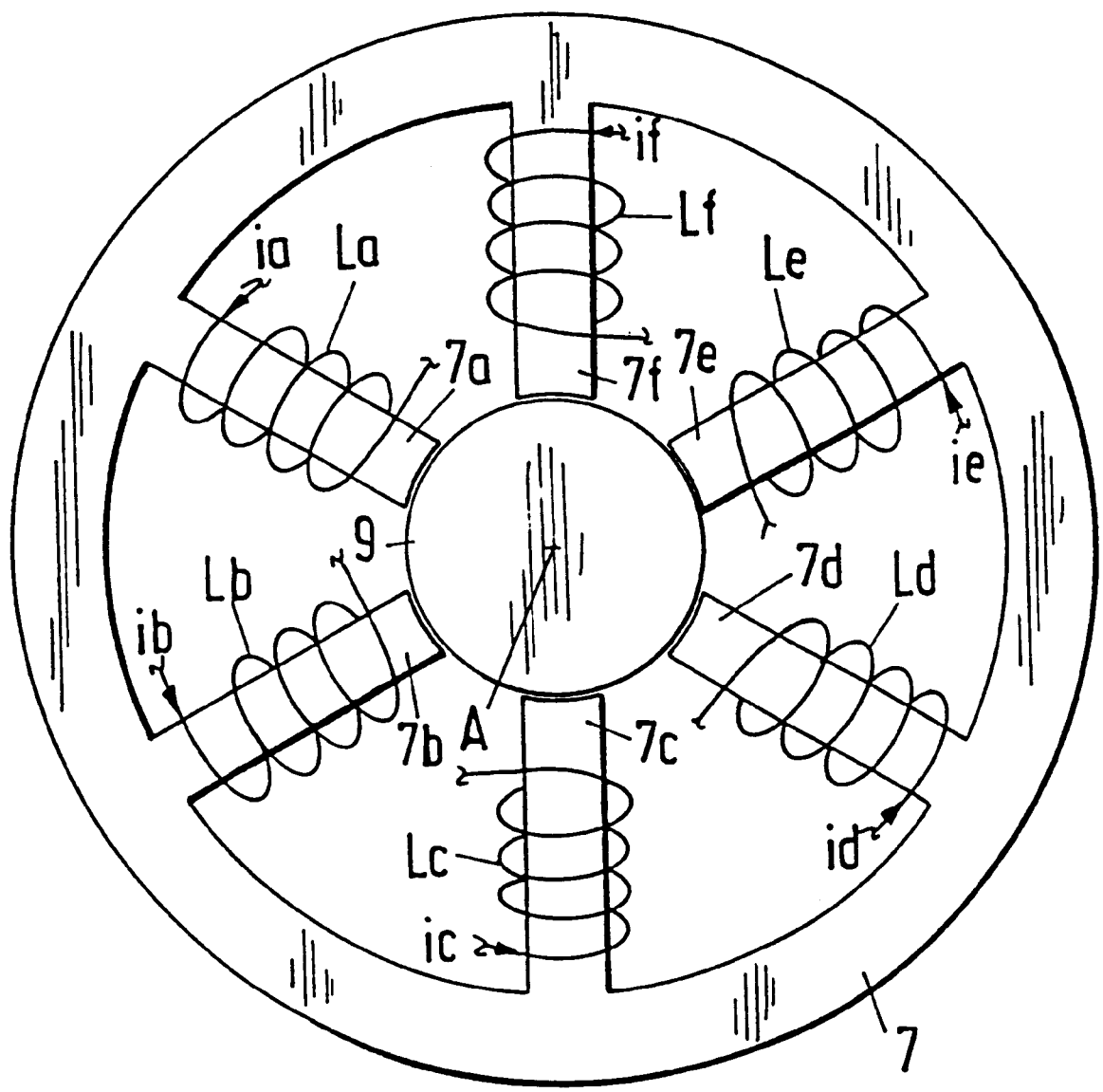
Figure 4B:
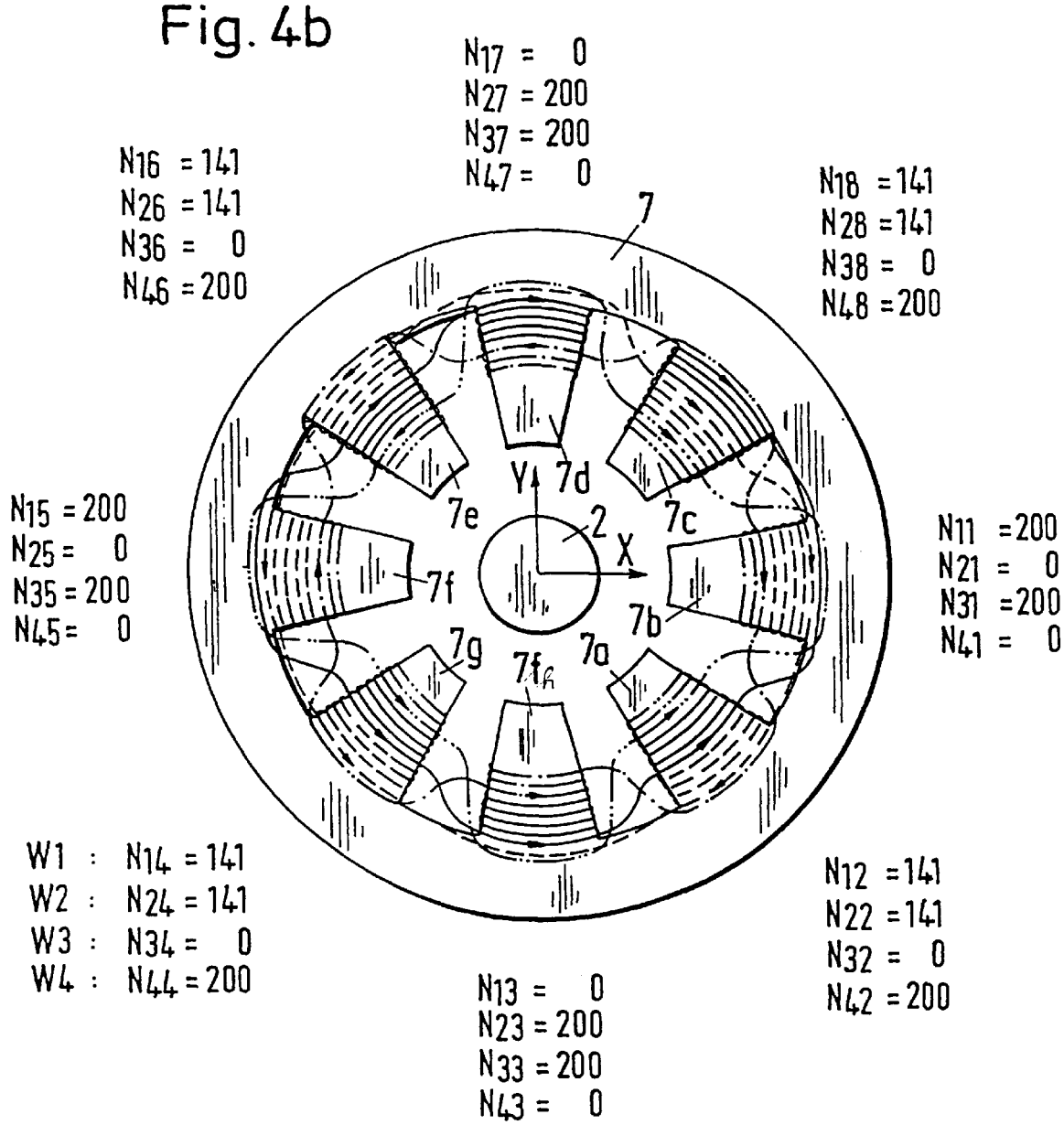
Figure 4D:
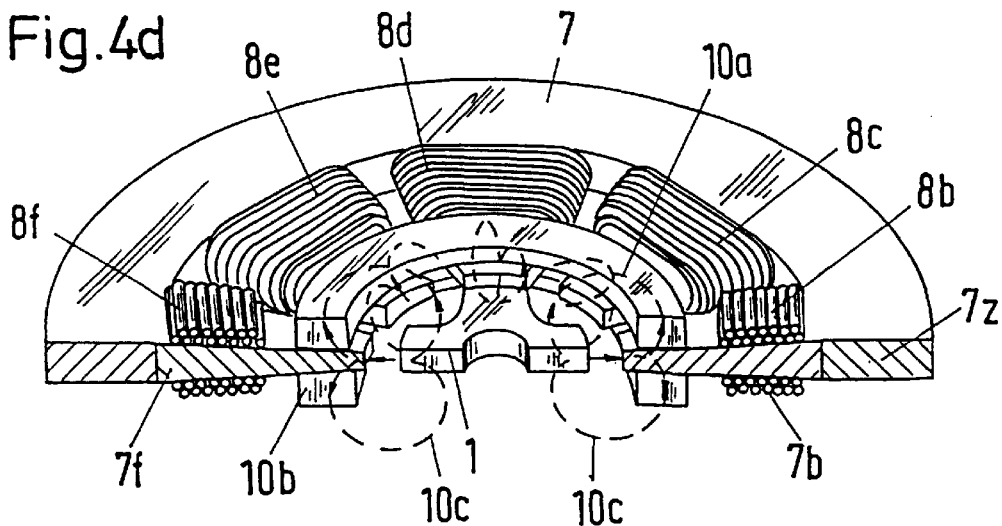
Figure 4H:
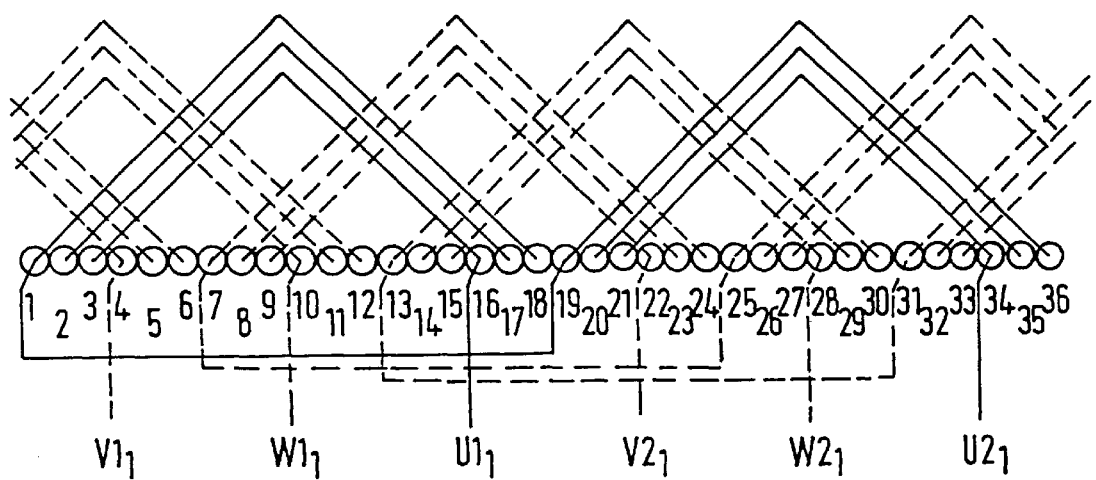
Figure 4I:
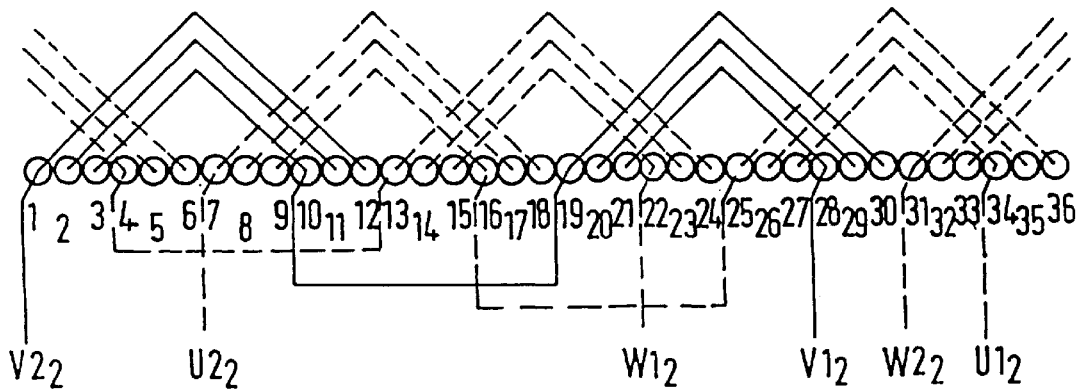
Figure 4E:
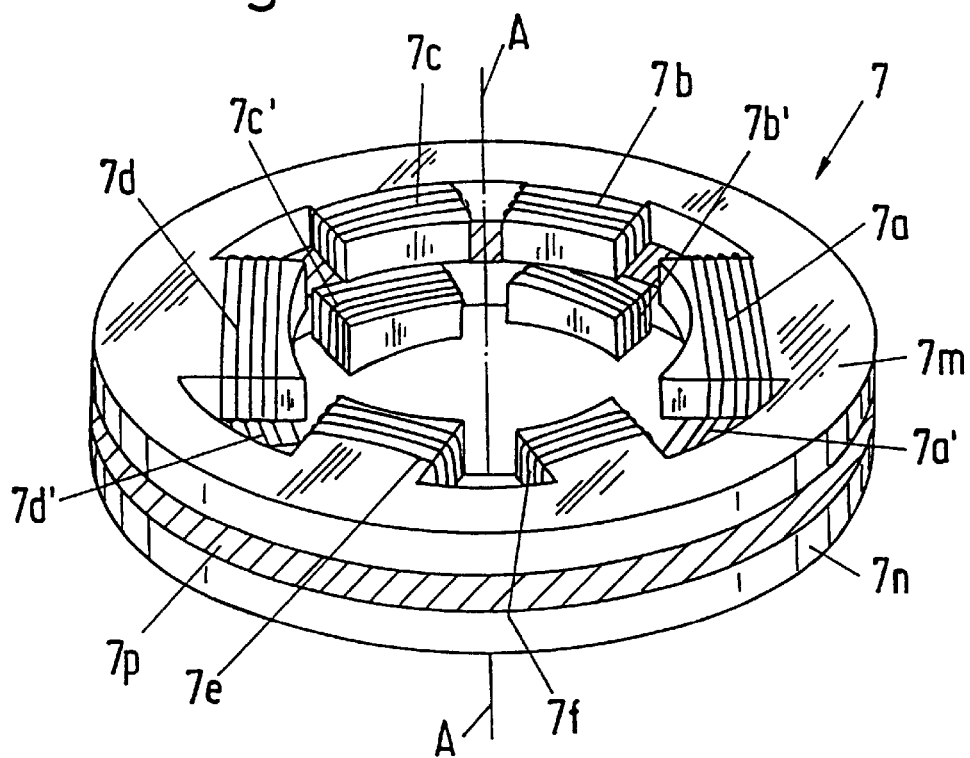
Figure 4F:
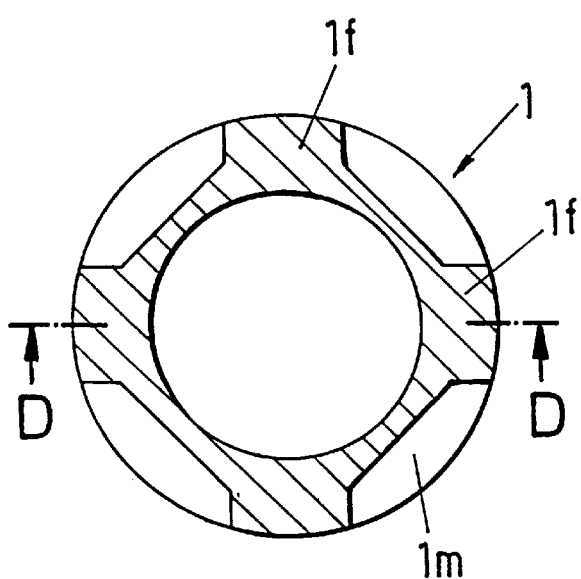
Figure 4G:
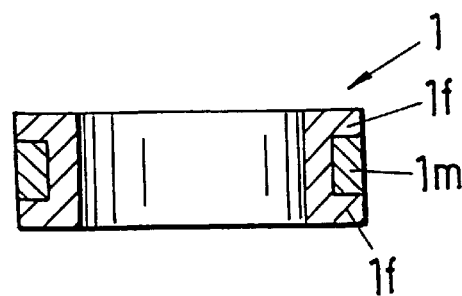
Figure 5A:
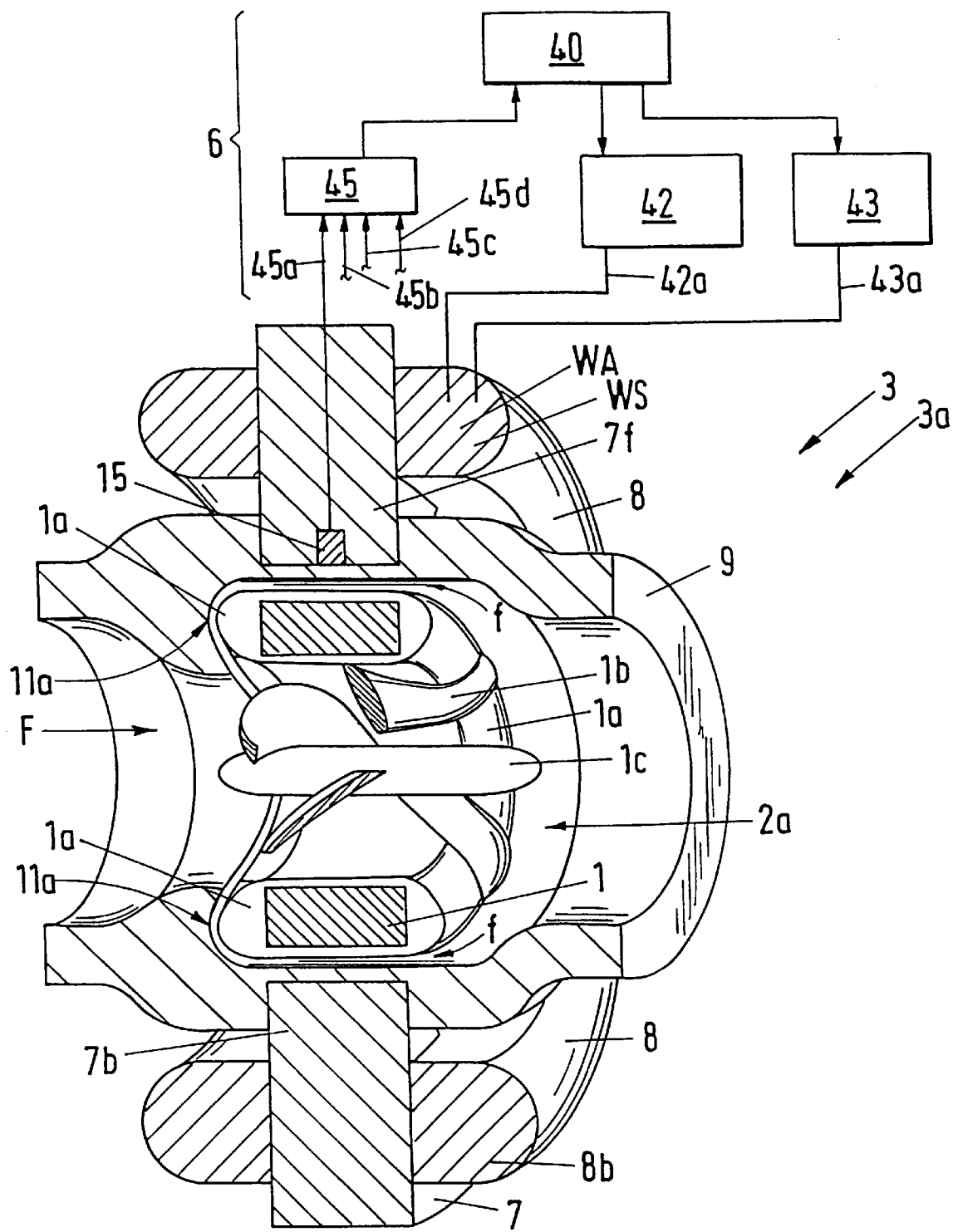
Figure 6A:
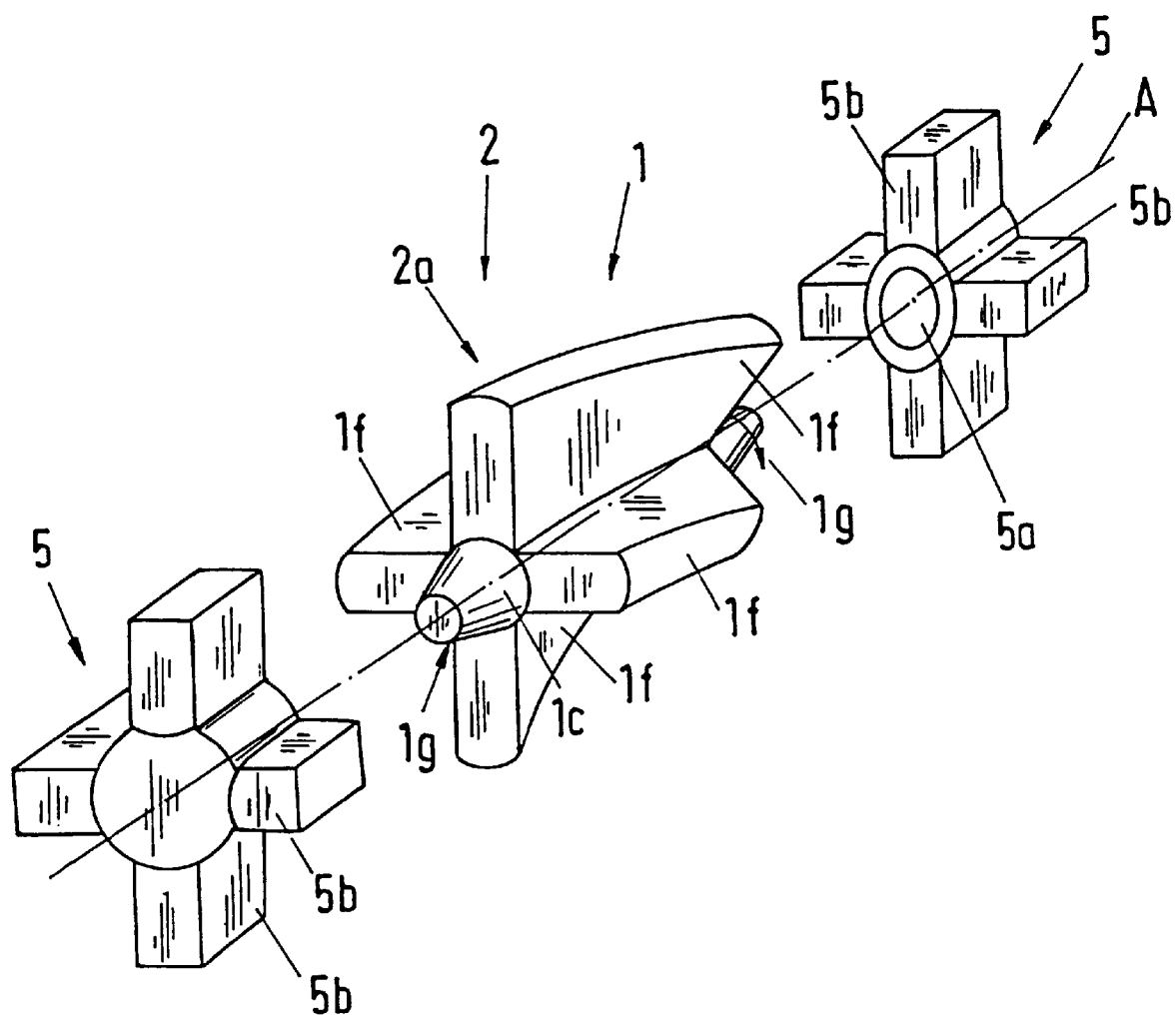
Figure 6B:
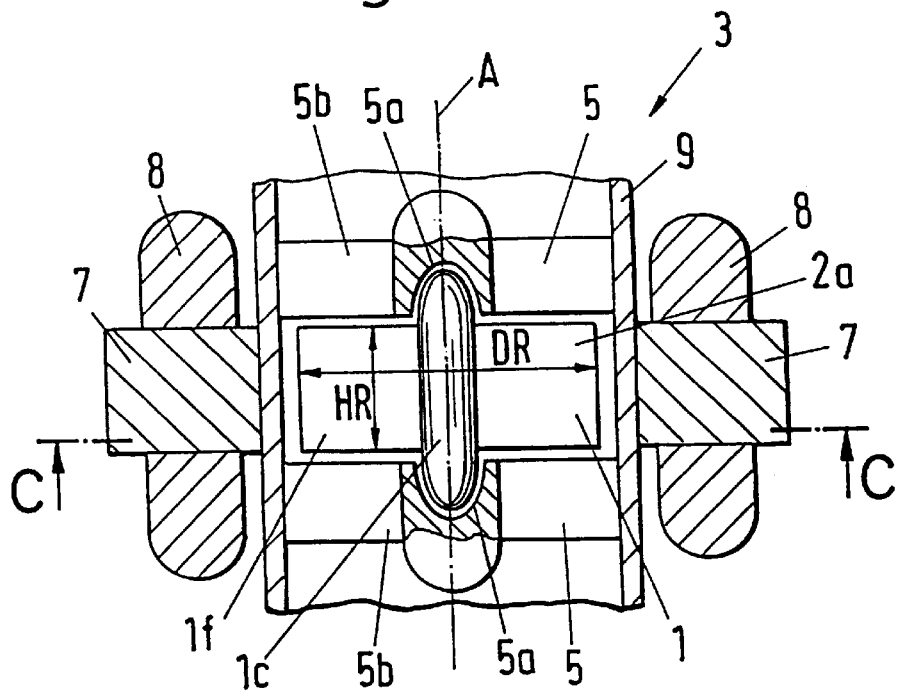
Figure 6C:
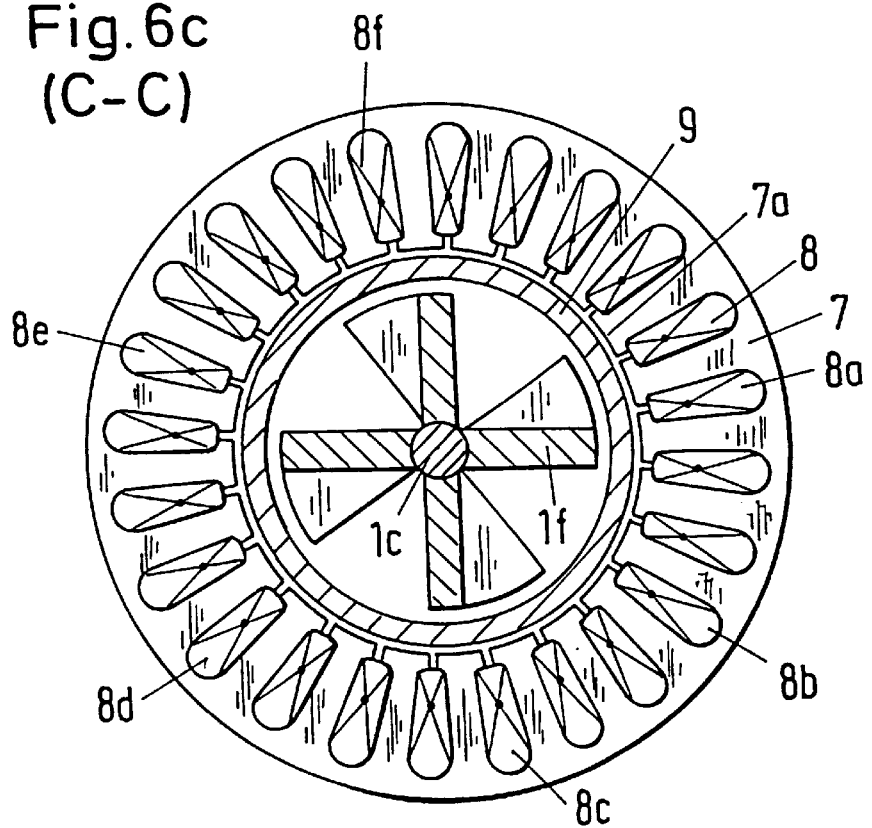
Figure 6D:
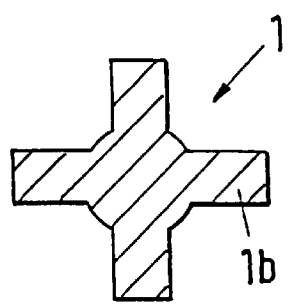
Figure 6E:
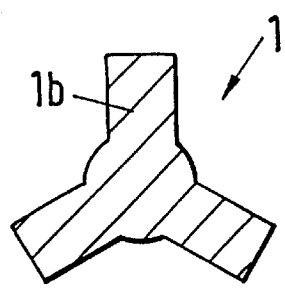
Figure 6F:
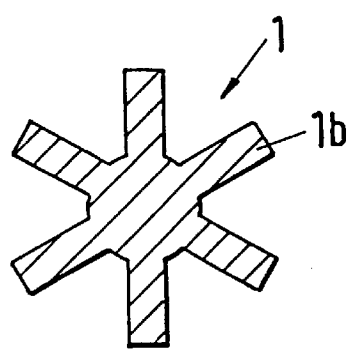
Figure 6G:
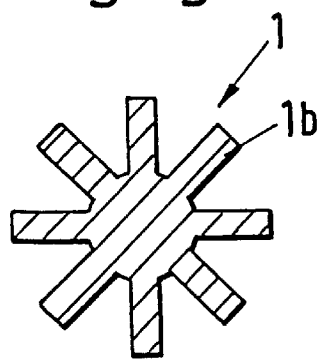
Figure 7:
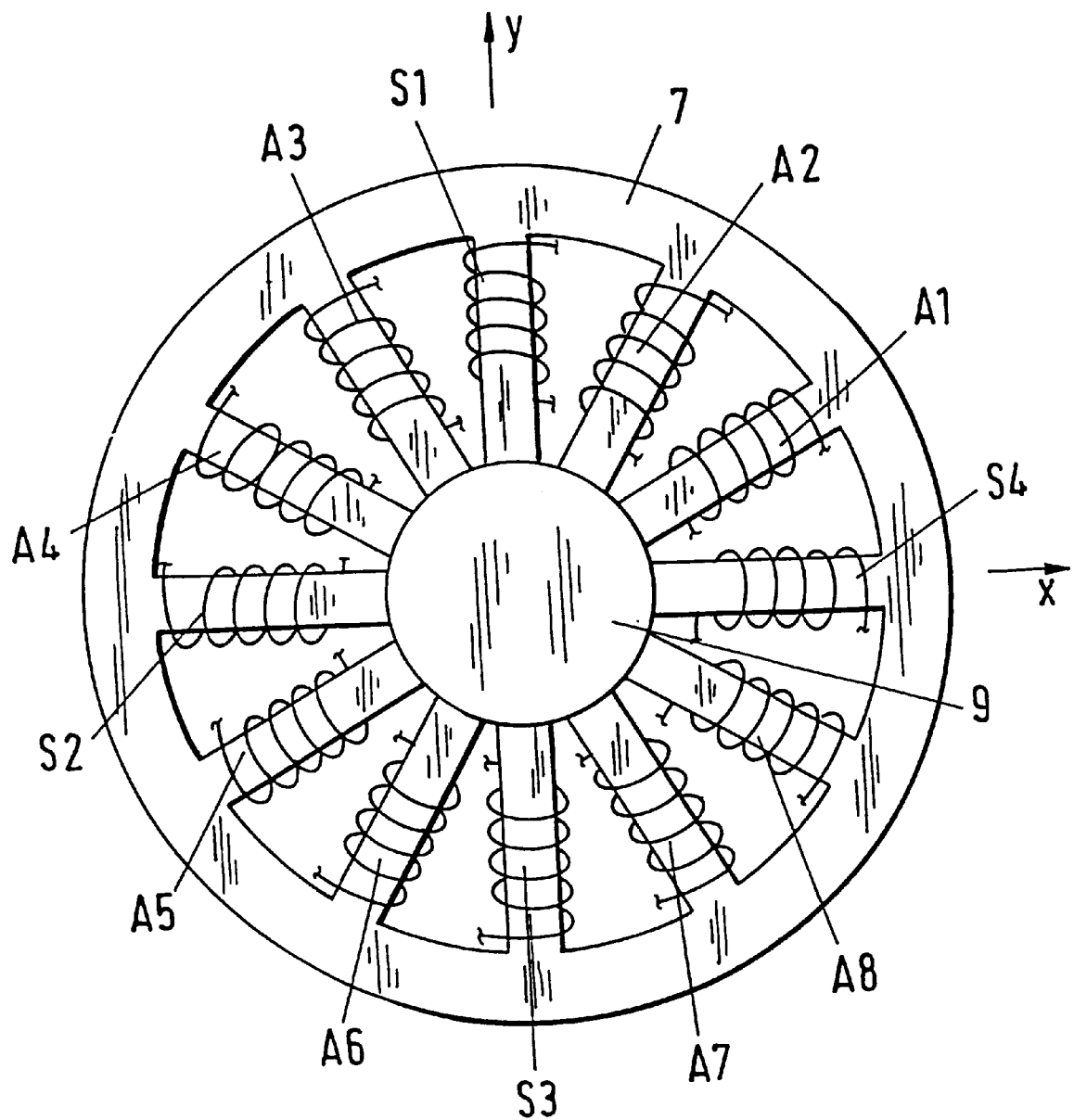
Figure 7A:
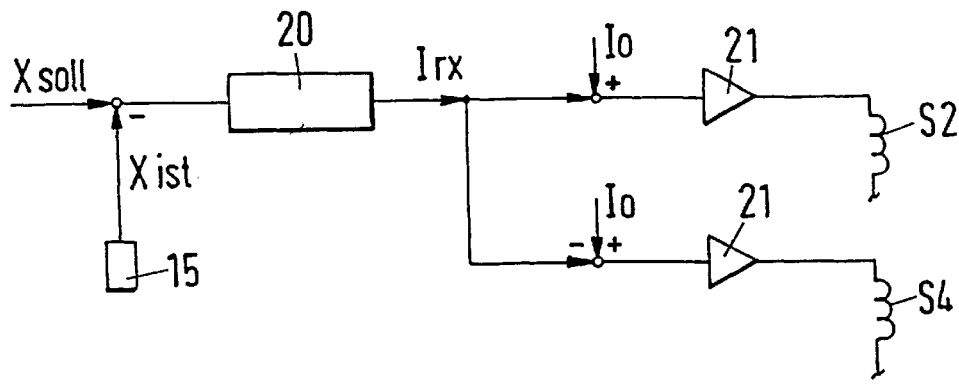
Figure 7B:
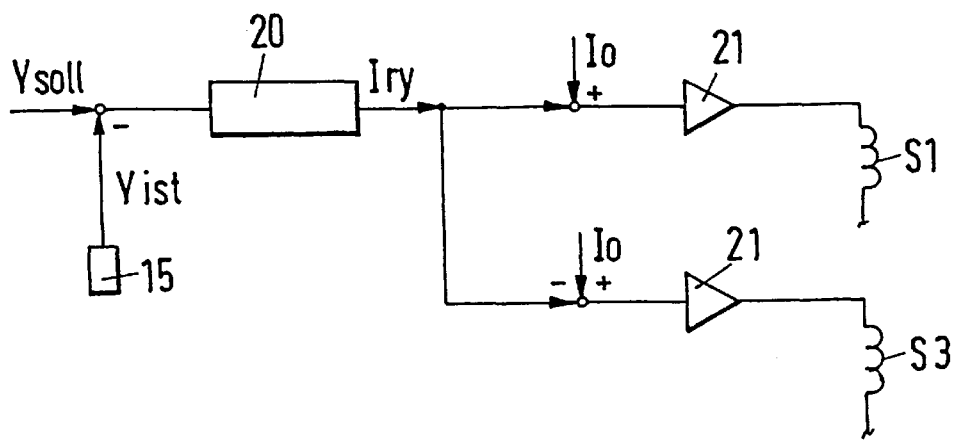
Figure 7C:
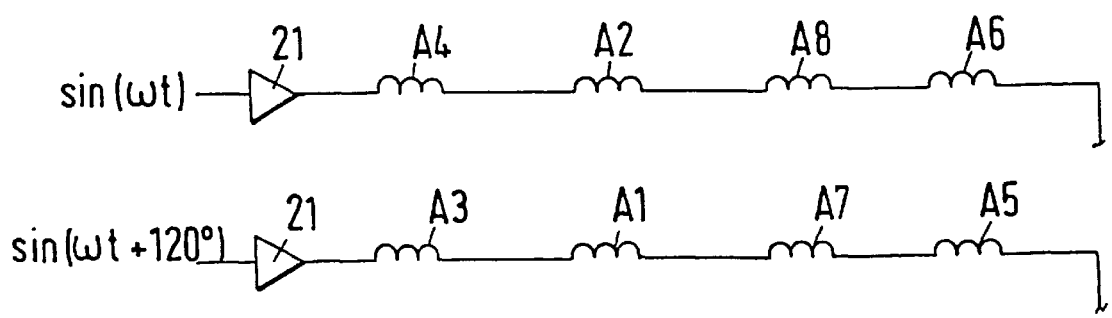
Figure 8C:
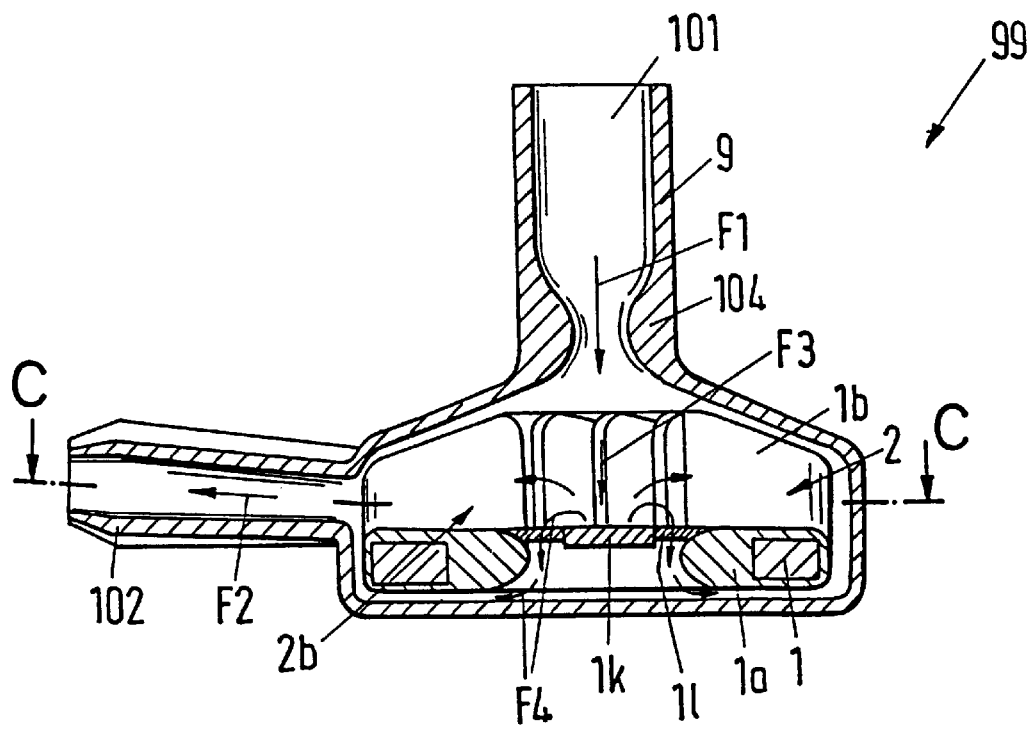
Figure 8D:
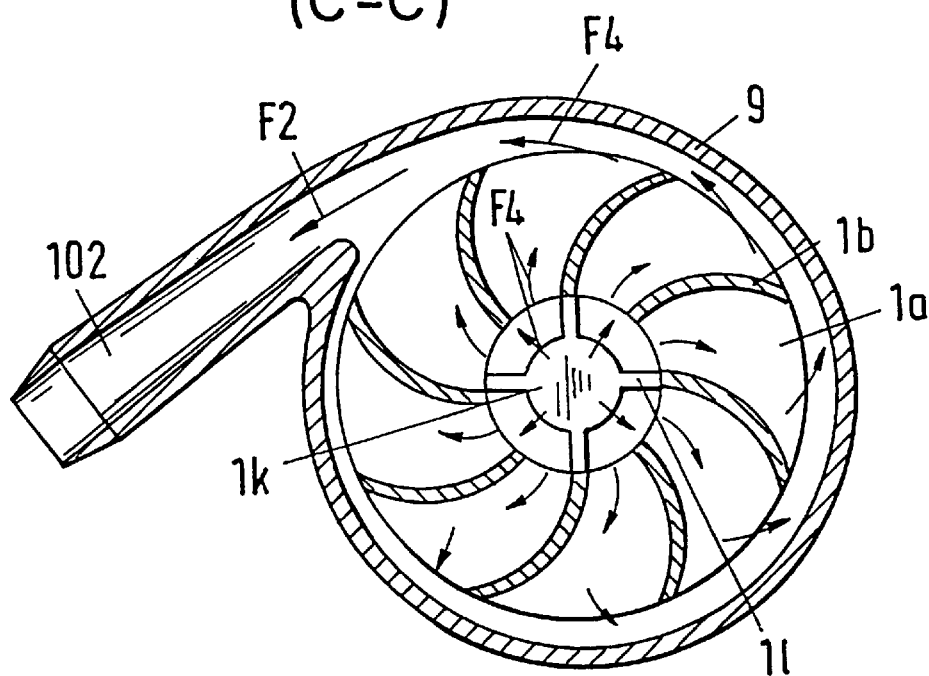
Figure 8E:
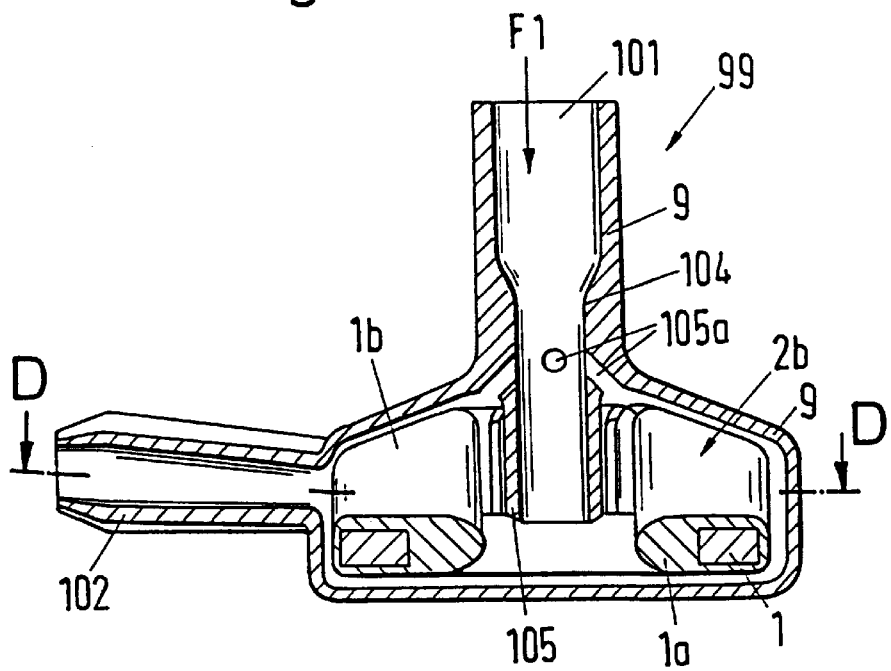
Figure 8F:
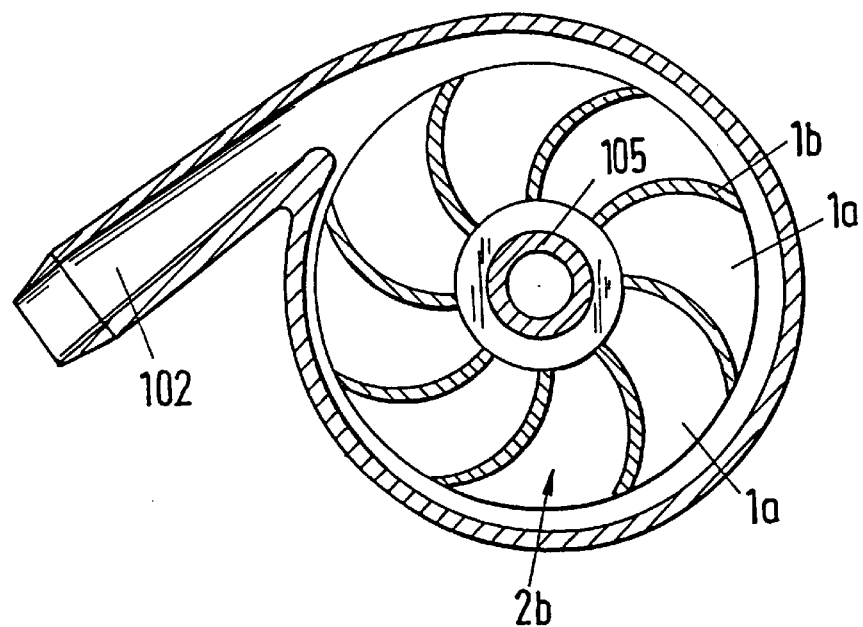
Figure 8G:
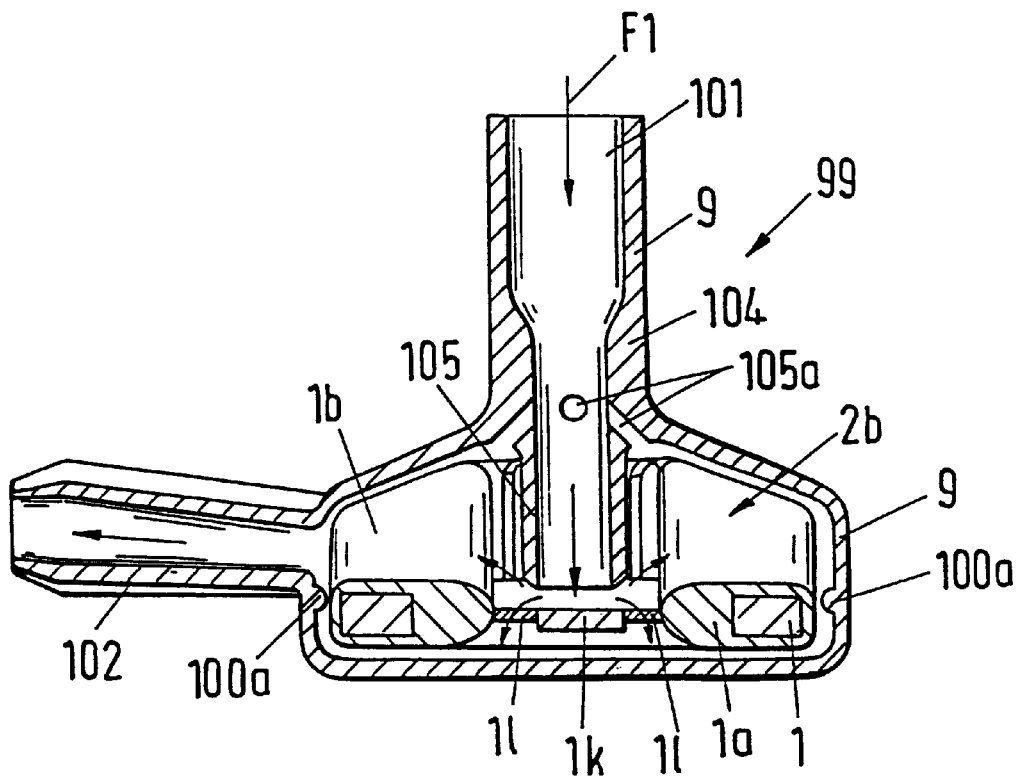
Figure 8H:
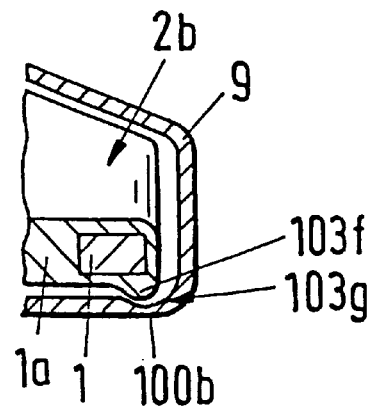
Figure 8K:
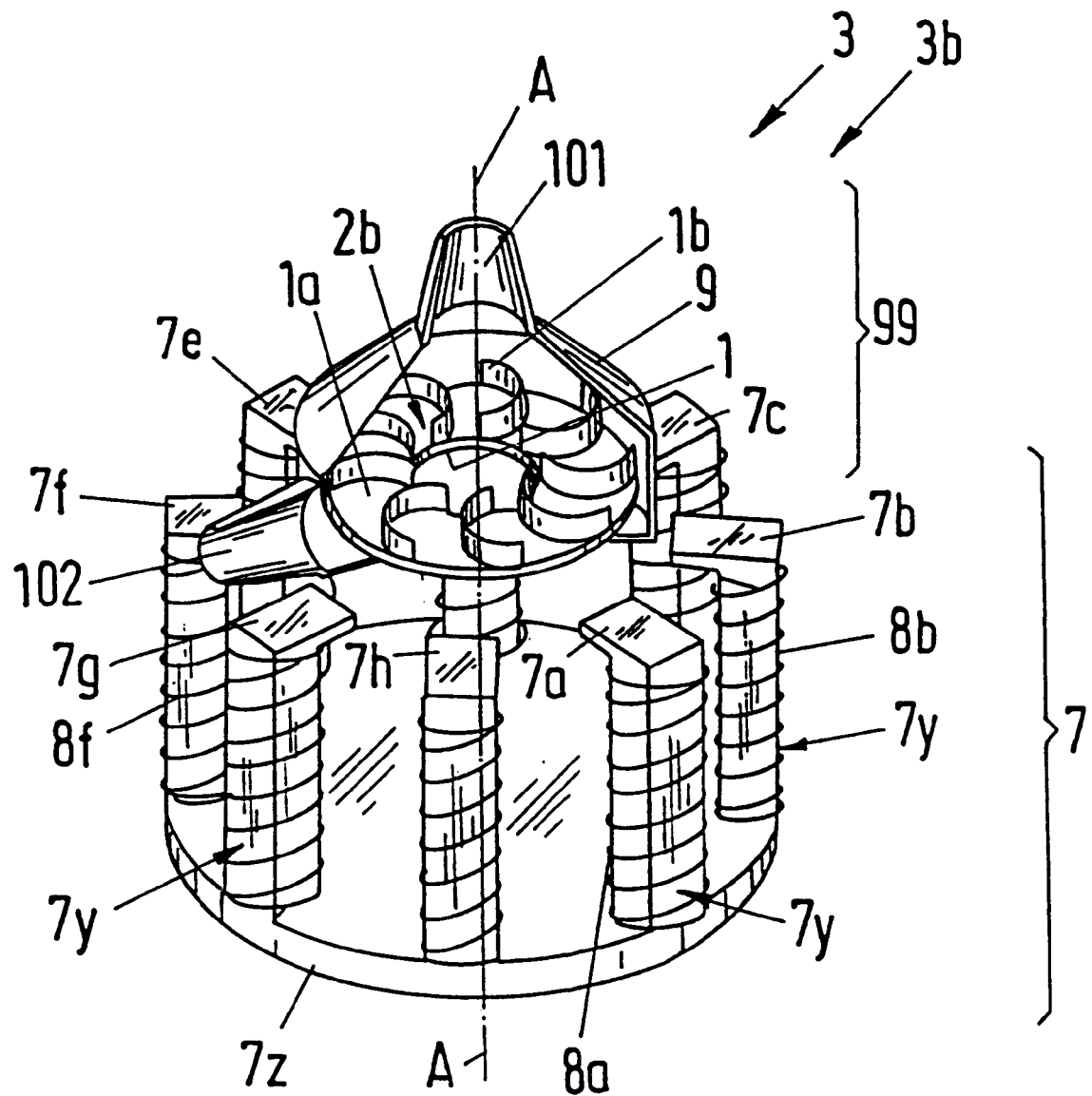
Figure 14A:
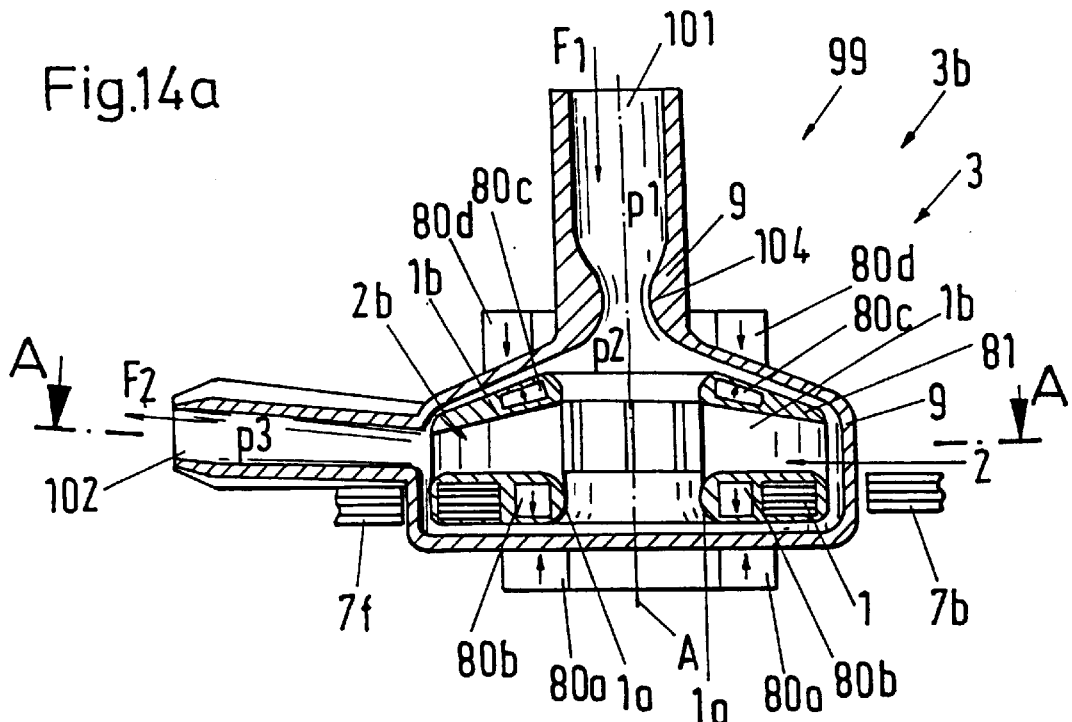
Figure 14B:
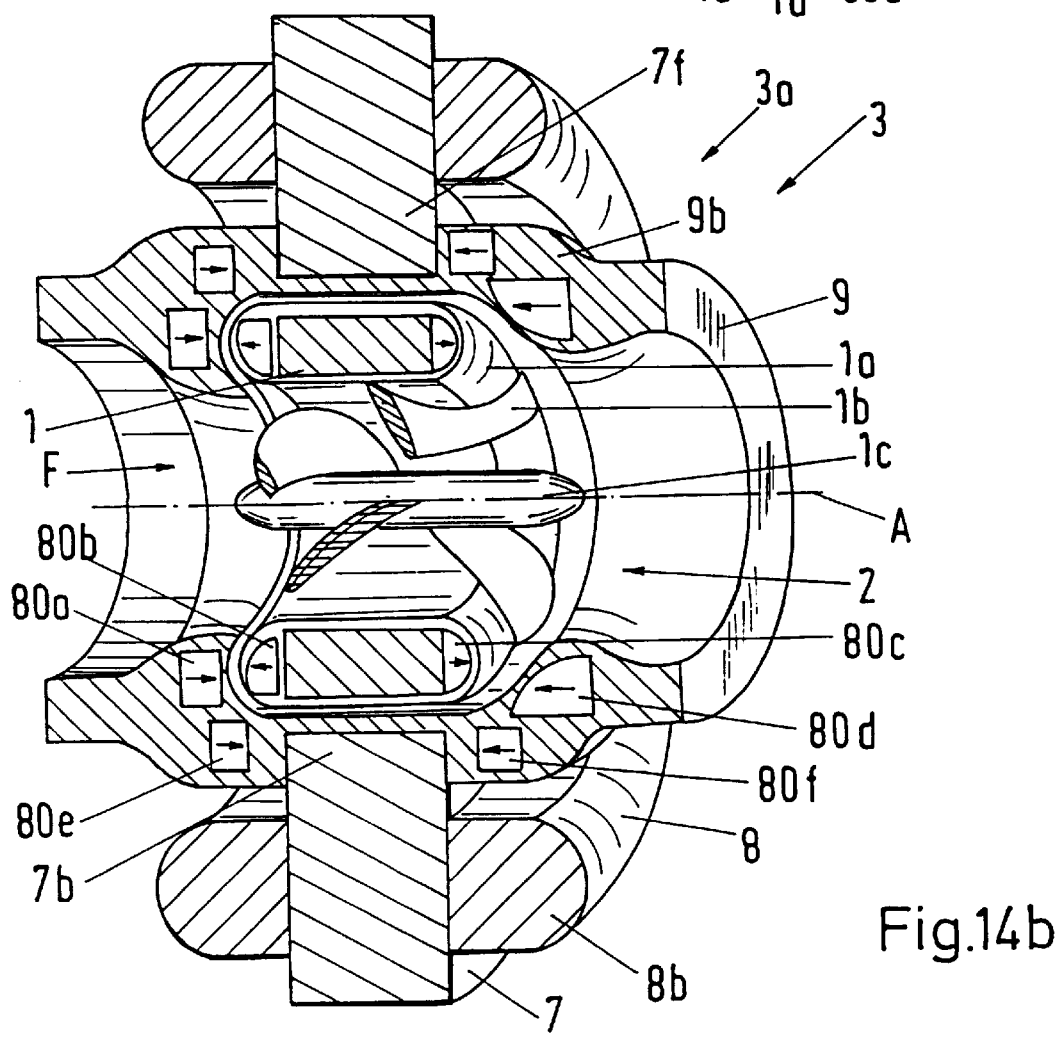

FIGS. 1b, 1c, and 1d show different positions of the magnetically effective rotor part relative to the stator of an axial or centrifugal pump;

FIGS. 2a, 2b, 2c, 2d, 2e, 2f, 2g, 2h show magnetically active rotor parts of different designs;

FIG. 3a is a section through an axial impeller along line A—A according to FIG. 3b;

FIG. 3b is a top view of the axial impeller according to FIG. 3a;

FIG. 3c is a section through the axial impeller along line B—B in FIG. 3a;

FIGS. 4a, 4b, 4d, 4e show embodiments of a stator for an axial or centrifugal pump;

FIGS. 4f, 4g show embodiments of a rotor for a stator that has a unipolar bearing;

FIGS. 4h, 4i show a winding diagram for a drive or control winding with a three-phase design;

FIG. 5a shows an embodiment of an additional hydrodynamically acting bearing device of an axial pump as well as a control device;

FIG. 6a shows an embodiment of an axial impeller designed as a reluctance rotor;

FIG. 6b is a lengthwise section through an axial pump comprising a reluctance motor;

FIG. 6c is a cross section through the reluctance motor according to FIG. 6b, along line C—C;

FIG. 6d, 6e, 6f, 6g, 6h show a cross section through various designs of axial impellers and reluctance rotors;

FIG. 7 is a top view of a stator for an axial or centrifugal pump;

FIGS. 7a, 7b, and 7c show an example of control of the coils of the stator according to FIG. 7;

FIG. 8a is a lengthwise section through a centrifugal pump along line B—B in FIG. 8b;

FIG. 8b is a cross section through the centrifugal pump according to FIG. 8a along line A—A;

FIG. 8i is a profile of the pressure of the fluid that develops between the housing and the rotor;

FIGS. 8c–8h show additional embodiments of a centrifugal pump part;

FIG. 8k shows a centrifugal pump with a stator designed as a temple motor;

FIG. 9 is a cross section through a magnetically effective rotor part;

FIGS. 10a, 10b, 11a, 11b, 13a, 13b show a top view and a side view of rotor parts made in the form of disks;

FIG. 14a is a lengthwise section through a centrifugal pump having a permanently magnetically effective compensation for axial thrust;

FIG. 14b is a lengthwise section through an axial pump having a permanently magnetically effective compensation for axial thrust.

FIG. 1 shows a lengthwise section through a rotary pump 3 according to the invention designed as an axial pump 3a, with a housing part 9 which has constrictions 9a, 9b. A stator 7 enclosing housing 9 in the circumferential direction is located outside housing 9, said stator having teeth 7b, 7f extending in the radial direction. These teeth 7b, 7f have their tips resting inside the jacket of housing part 9 in such fashion that a housing section is located between the tips of teeth 7b, 7f and the interior of housing 9, so that the interior of housing 9 is completely separated from stator 7. Stator 7 with teeth 7b, 7f is made of a ferromagnetic material. Teeth 7b, 7f are wound with coils 8b, with the totality of the windings 8 being shown. Within housing 9, rotor 2 designed as an axial wheel 2a, also called the axial impeller, is located. This axial impeller 2a in the embodiment shown consists of an annular permanent magnet 1, magnetized in the radial direction, said magnet being surrounded by a rotor jacket 1a made of plastic. Within the circular recess in magnetically effective rotor part 1, hydrodynamically active blades 1b as well as a middle part 1c that extends in axial direction A relative to axial impeller 2a are located. Blades 1b extend in axial direction A beyond rotor jacket 1a up to the outer surface of rotor jacket 1a facing stator 7. Blades 1b together with middle part 1c form an impeller that is favorable for generating an axial flow, with the impeller advantageously having a diameter that is as large as possible in order to produce a high pumping power. Advantageously, blades 1b are located not only so that they extend inside the inside diameter of rotor part 1 but also, as shown in FIG. 1, extend in axial direction A, projecting beyond rotor jacket 1a, up to a point close to the wall of housing 9. As a result, nearly the entire diameter of the interior of housing 9 is used for locating the impeller and/or for delivering the fluid. Rotor jacket 1a as well as blades 1b and middle part 1c as well as housing 9 are made of a non-ferromagnetic material such as plastic, a metal such as titanium, a ceramic, or a biocompatible material such as polycarbonate. Axial impeller 2a is held by magnetically active rotor part 1 with zero contact inside housing 9 by virtue of the magnetically active forces of stator 7, with a torque acting on rotor part 1 being capable of being produced to drive axial impeller 2a, causing it to rotate around rotation axis A. Not shown are sensors 15 for detecting the position of axial impeller 2a and/or rotor part 1. These sensors 15 are preferably located either outside housing 9 or inside the jacket of housing 9 in order to measure the position of rotor part 1 or the magnetic flux with zero contact. An eddy current sensor, an inductive sensor, or a Hall element with a permanent magnet are suitable as the measuring principle for sensors 15. The position of axial impeller 2a can be controlled with zero contact in a plane that runs approximately perpendicularly to rotational axis A, by an appropriate control of windings 8a, 8b, 8c, 8d, 8e, and 8f located in stator 7. The windings comprise a drive winding WA with a pole pair number p and a control winding WS with a pole pair number p+1 or p−1.

FIG. 1a shows a perspective view of a section through a stator 7 as well as a magnetically active rotor part of rotary pump 3, designed as an axial pump 3a or centrifugal pump 3b. The magnetically ineffective parts of rotary pump 3, such as housing 9 or rotor jacket 1a and blades 1b, are not shown for improved understanding of the arrangement. Stator 7 has an annular part designed as an iron return 7z, on which teeth 7b, 7c, 7d, 7e, 7f are mounted so that they extend in the radial direction. Iron return 7z and teeth 7b, 7c, 7d, 7e, 7f consist of a ferromagnetic metal. The magnetically effective rotor part 1, as shown in FIG. 2a and 2b, consists of an annular permanent magnet polarized in the radial direction. Coils 8b, 8c, 8d, 8e, and 8f have two partial windings designed so that they can be controlled independently of one another, with one partial winding being designed as a drive winding WA with a pole pair number p and the other partial winding being designed as a control winding WS with a pole pair number of p+1 or p−1. Such an arrangement of the windings is shown in detail in FIG. 4b. Drive winding WA and the magnetically effective part of rotor 1 cooperate in a manner comparable to a synchronous machine, in which a magnetic rotary field is generated in drive winding WA, designed with two phases, in stator 7, said rotary field being followed by rotor 1 so that rotor 1 is driven to rotate around its axis A. The position of rotor 1 is detected by sensors 15, not shown, and the control windings WS, designed to be three-phase, in view of the magnetic field generated by drive winding WA, are controlled in such fashion that rotor 1 is kept in a plane perpendicular to axis A and therefore with zero contact in stator 7 in the x and y directions. Rotor 1 is thus actively controllable with respect to three degrees of freedom, namely its position in the x and y directions as well as rotation around axis A.

In a side view of FIG. 1a, FIG. 1b shows rotor 1 in a normal position between stator teeth 7b and 7f, with rotor part 1 having a diameter DR and a height HR, and with stator tooth 7f or 7b on the side facing rotor part 1 having a height HS, and with the gap between stator tooth 7f or 7b and rotor 1 having a distance DL. FIG. 1c shows rotor 1 deflected from the normal position in direction z. Permanent-magnetic rotor 1 creates a magnetic field which begins in rotor 1 and extends through the air gap to stator tooth 7b, and returns to rotor 1 through iron return 7z, stator tooth 7f, and the air gap, with a portion of the total magnetic flux also passing through stator teeth 7c, 7d, and 7e. When rotor 1 is deflected from the normal position in the z direction, this permanent-magnetically pretensioned flux circuit, produces a passively acting restoring reluctance force Ftot, composed of a component Fz extending in the z direction and a component Fx extending in the x direction. Force component Fz has a stabilizing effect on the position of rotor 1, since the latter always acts in the direction opposite to the deflection when rotor 1 is deflected in the z direction, and tends to return rotor 1 to the normal position.

FIG. 1d shows rotor 1 in a tilted position relative to the y axis. In this position, a passively acting restoring reluctance force Ftot exerts a torque on rotor 1 that opposes the tilting, so that the restoring force component Fz has a stabilizing effect on the position of rotor 1 and tends to return rotor 1 to the normal position. The same restoring effect applies when rotor 1 is tilted around the x axis. Thus, the position of rotor 1 is stabilized by passively acting reluctance forces with respect to three degrees of freedom, namely a translational movement in the z direction as well as tilting around the x and y axes. Rotor 1 is thus mounted with zero contact in stator 7 by magnetically acting forces and can be driven by a motor around its axis A, with three degrees of freedom of the position of rotor 1 being controllable, and the three additional degrees of freedom of the position of rotor 1 being kept in a stable position by passively acting reluctance forces. In order for these passively acting reluctance forces to develop, rotor part 1 and the shape of teeth 7b, 7c, 7d, 7e, 7f of stator 7 must be formed and mutually arranged in corresponding geometrically patterns. Teeth 7b, 7c, 7d, 7e, 7f on the side facing rotor 1 preferably have a height HS equal to height HR or approximately equal to height HR of rotor part 1. The diameter DR of rotor part 1 is designed to be more than twice the height HR of rotor part 1. By virtue of this mutually adapted geometric design and arrangement of stator 7 and rotor 1, the restoring, passively acting, reluctance forces are made possible. These passively acting reluctance forces can be increased by a slight distance DL, with this distance, as shown in FIG. 1, being determined by the thickness of housing wall 9 and rotor jacket 1a. The passively acting reluctance forces can likewise be increased by permanent-magnetic pretensioning of the magnetic circuit, for example with an additional coil or an additional permanent magnet being located in stator 7 to increase the magnetic flux through rotor part 1.

In axial pump 3a according to the invention, a thrust acting in the axial direction or in the z direction is exerted on the fluid delivered in flow direction F. This thrust, which engages axial impeller 2a in the z direction, must be compensated by a passive reluctance force acting in the opposite direction. Therefore the passive reluctance force Fz acting maximally in the z direction is of critical importance for operating axial pump 3a, since when this maximum force is exceeded, rotor part 1 is torn out of equilibrium in stator 7. To avoid such a tearing free of rotor part 1, housing 9 according to the embodiment in FIG. 1 has constrictions 9a, 9b that limit the freedom of movement of axial impeller 2a in axial direction A. In the event of a severe deflection of the axial impeller in the z direction, axial impeller 2a would come in contact with housing 9 in the vicinity of constrictions 9a and 9b, so that the maximum deflection is limited. The magnetically effective rotor part 1 remains in the magnetically effective influence range of stator 7 so that axial impeller 2a can be returned to the normal position by magnetically acting forces.

In a top view, FIG. 2e shows another annular rotor part 1 with two pole pairs or two south poles S and two north poles N. FIG. 1f shows a side view of the rotor part in FIG. 2e, with two pole pairs and four poles S, N. FIG. 2c shows another embodiment of a rotor part 1 that comprises four shell magnets 1d, which are arranged so that they contact an annular iron return 1e, with the outer surfaces of rotor part 1 or of shell magnet 1d alternately forming a south pole S and a north pole N. FIG. 2d shows a section through the middle of rotor part 1 according to FIG. 2c with shell magnet 1d and iron return 1e.

FIG. 3a shows a lengthwise section through an axial impeller 2a, as used in the embodiment according to FIG. 1. The magnetically effective rotor part 1 is designed as a permanent magnet like that shown in FIGS. 2a and 2b. Rotor part 1 is enclosed by a jacket 1a and also has blades 1b with middle part 1c, permanently attached to rotor part 1. Blades 1b are designed hydrodynamically such that a thrust acting on a fluid in axial direction A can be produced. FIG. 3b shows a top view of axial impeller 2a according to FIG. 3a, with rotor jacket 1a, the path of blades 1b, and middle part 1c being visible. FIG. 3c shows a section along line B—B according to FIG. 3a. The annular path of magnetically active rotor part 1 can be seen from FIG. 3c, as well as blades 1b that run especially inside the ring, and middle part 1c.

FIG. 4b shows winding 8 of stator 7 according to the embodiment in FIG. 1 in detail. On teeth 7a, 7b, 7c, 7d, 7e, 7f, 7g, 7h of stator 7 is a two-phase drive winding WA (windings W1 and W2), with a pole pair number of 1 for producing a magnetic rotary field as well as a two-phase control winding WS with a pole pair number 2 (windings W3, W4) for controlling the position of rotor 2 in the x and y directions. Drive winding WA has a pole pair number p=1 and control winding WS has a pole pair number p=2. Nxx represents the number of turns of individual windings W1, W2, W3, W4 for one embodiment, with N11, N12, and N13, also designated N1x, representing the number of turns of winding W1 on teeth 7a, 7b, 7c, 7d, 7e, 7f, 7g, or 7h. In addition, N2x, N3x, and N4x represent the corresponding numbers of turns on windings W2, W3, and W4 on the corresponding teeth.

The upper part of FIG. 5a shows a control device 6 for controlling rotary pump 3, made in the form of an axial pump 3a according to the embodiments in FIG. 1 and FIG. 5a. The position of axial impeller 2a is determined by a sensor 15 located on the surface of tooth 7f, with the sensor signal being supplied through a signal lead 45a to a signal evaluating device 45, said evaluating device 45 evaluating the signals from additional sensors, not shown, for monitoring axial impeller 2, said signals being supplied through signal leads 45b, 45c, and 45d, in order to determine the position as well as the rpm of axial impeller 2 in housing 9. The values are supplied to a regulating device 40 which includes a microcomputer, with regulating device 40 calculating a setpoint for the drive and control windings, and supplying these setpoints to current controller 42 of control winding WS as well as to current controller 43 of drive winding WA. Control winding WS is connected by an electrical lead 42a with current controller 42 and drive winding WA is connected by an electrical lead 43a with current controller 43.

FIG. 4a shows another embodiment of a stator 7 with six teeth 7a, 7b, 7c, 7d, and 7e, extending in the radial direction, said teeth having individually controllable coils La, Lb, Lc, Ld, Le, and Lf. A magnetically effective rotor part 1, not shown but designed according to FIG. 2a, is located inside housing 9. Each of coils La, Lb, Lc, Ld, Le, and Lf is connected with an adjusting device, with the coils being controlled by a superior control device 40 in such fashion that rotor 1 is held with zero contact relative to a plane that runs perpendicularly to rotation axis A, and a driving torque is also exerted on rotor 1.

Stator 7 according to FIG. 4a, like stator 7 according to FIG. 1a, can also be operated to function as a reluctance motor, in which a rotor 1 designed according to FIG. 2g for example is used. This cruciform projecting rotor part 1 that has partial sections 1f and is magnetically effective is ferromagnetic but is not permanently magnetized. The rotation of rotor 1 around rotation axis A is produced by reluctance forces, with the individual coils La, Lb, Lc, Ld, Le, and Lf being correspondingly controlled sequentially in time. Rotor 1 is also kept suspended with zero contact by a corresponding control of coils La, Lb, Lc, Ld, Le, and Lf. FIG. 2h shows a lengthwise section through cruciform rotor 1 according to FIG. 2g.

FIG. 4d shows another embodiment of a rotor part 1 that is magnetically effective and is held and driven with zero contact by a stator 7. Rotor part 1 is designed as a synchronous reluctance rotor in a design according to FIG. 2g or FIG. 6f. In the end areas of teeth 7a, 7b, 7c, 7d, 7e, and 7f, a permanent magnet 10a, 10b is located on both sides of said teeth, said magnetic being annular in shape and polarized in axial direction A. These permanent magnets 10a, 10b generate a unipolar flux indicated by field lines 10c, with the magnetic unipolar flux passing through rotor 1 and teeth 7a, 7b, 7c, 7d, 7e, and 7f extending outward in the radial direction.

By virtue of this unipolar flux, the passively acting reluctance force or the restoring force Ftot shown in FIGS. 1c and 1d is increased so that rotor 1 is more stably mounted in stator 7 or a higher thrust acting in axial direction A can be produced by axial impeller 2a. In this case, control winding WS can be made with two poles and drive winding WA can be made with four or six poles. In addition, with the flow through the windings kept constant, increased torque and increased radial bearing forces can be produced.

FIG. 4e shows another embodiment of a stator 7 which has an additional unipolar flux for more stable mounting of rotor 2. Stator 7 consists of a first stator part 7m with teeth 7a, 7b, 7c, 7d, 7e, and 7f each of which has a winding and of a second stator part 7n with teeth 7a',7b',7c',7d',7e',7f' each of which has a winding, as well as a permanent magnet 7p polarized in axial direction A, said magnet being annular in shape and located between the two stator parts 7m, 7n. FIG. 4f, in a top view, and FIG. 4g, in a sectional view along line D—D, show an embodiment of a rotor part 1 for stator 7 according to embodiment 4e. Rotor part 1 comprises a cylindrical iron part with parts 1f projecting in a cruciform manner, so that as can be seen from FIG. 4g, a ferromagnetic rotor part 1 made in the shape of a U facing the teeth of stator 7 is obtained. The sensor ring n inserted into the groove thus formed consists of a non-ferromagnetic metal. A unipolar magnetic flux is developed In rotor part 1 inserted in stator 7 according to FIG. 4e, said flux starting at permanent magnet 7p through teeth 7a, 7b, 7c, 7d, 7e, 7f, and 7g and extending to rotor part 1 and from the latter through teeth 7a', 7b', 7c', 7d', 7e', 7f', and 7g' back to permanent magnet 7p. This unipolar flux produces a stabilizing effect with respect to deflection of rotor part 1 in axial direction A. In combination with a winding of pole pair number 1 as well as a regulating device, the radial position of the rotor can be stabilized. If the windings-of pole pair 1 in first stator part 7m and in second stator part 7n can be controlled separately by an appropriate control of these windings, tilting of rotor 1 can be stabilized actively, in other words in a regulated fashion. A torque can be generated by one winding with the same pole pair number as the rotor. Sensors 15 for detecting the position of rotor 1 can be located so that they lie in the axial direction between the two stator parts 7n and 7m.

FIG. 5a shows an arrangement for increasing the thrust of axial impeller 2a. Housing 9, on the left side, has a partial area lla designed to match the geometry of rotor jacket 1a, said area together with rotor jacket 1a forming a hydrodynamic axial bearing that acts in axial direction A. The fluid which is under high pressure on the right side of axial pump 3, especially a liquid, flows back in a partial flow f between axial impeller 2a and housing 9 in flow direction f to the left side of axial pump 3, which is the intake side, with a hydrodynamic axial bearing being formed at least in partial area 11a. In addition, the gap between axial impeller 2a in housing 9 in the vicinity of stator 7 can be made sufficiently wide that a bearing gap is obtained in this area also for a hydrodynamic radial bearing of axial impeller 2. The hydrodynamic or fluid dynamic bearing shown in FIG. 5a exerts an additional stabilizing effect on axial impeller 2a so that axial impeller 2a, even with relatively high forces acting on axial impeller 2a, is mounted securely and with zero contact relative to housing 9.

An additional bearing of axial impeller 2 that provides magnetic support in a hydrodynamic or fluid dynamic fashion inside housing 9 can be achieved by a number of embodiments. For example, rotor jacket 2 can have a groove on the outer surface facing stator 7, said groove running helically so that a hydrodynamically active step bearing is formed. By virtue of this measure, the flow of fluid f flowing from the pressure side to the intake side is also increased, reduced, suppressed, or deflected, since the fluid located in the gap is delivered depending on the pitch of the helical groove as well as the direction of rotation and the rpm of the rotor. With similar grooves provided on the front of the rotor, the effect of the hydrodynamic bearing acting in the axial direction can likewise be improved.

FIG. 6a shows an axial impeller 2a for a stator 7 that operates on the principle of a reluctance motor. Magnetically active rotor part 1 also forms axial impeller 2a, with rotor part 1 being made of a ferromagnetic material but not being permanently magnetized, and with section 1f of rotor part 1 that projects in a cruciform manner having a twist in axial direction A so designed that sections 1f also form blades 1b of axial impeller 2a. The path of sections 1f is correspondingly hydrodynamically optimized so that a thrust acting on the fluid in the axial direction can be produced by these sections 1f. The diameter DR of axial impeller 2a is at least twice as great as the axial height HR of axial impeller 2a. Axial impeller 2a is drivable and held with zero contact in stator 7 by magnetically acting forces. In addition to axial impeller 2a, an emergency bearing device 5 is provided with spacing on both sides in axial direction A. In the event of failure of the magnetic bearing or with very high thrusting forces in the axial direction, axial impeller 2a will be held in an emergency bearing position 5a by emergency bearing parts 1g projecting in the axial direction. Emergency bearing device 5 has ribs 5b arranged in a cruciform manner or guide blades 2b which are in an active relationship with housing wall 9 and are held by the latter. Ribs 5b form a pump stator or guide blades. FIG. 6b shows a lengthwise section through an axial pump 3, with an axial impeller 2a being shown in FIG. 6a. Axial pump 3 has a housing 9 surrounded by a stator 7 with coils 8. Magnetically active rotor part 1 with blades 1b and middle part 1c is mounted and drivable with zero contact Inside housing 9, with two emergency bearing devices 5 being located offset in the axial direction A next to rotor part 1 or next to axial impeller 2a. Magnetically active rotor part 1 has a diameter DR more than twice the height HR of rotor part 1. FIG. 6c shows a cross section through axial pump 3 according to FIG. 6b along line C—C. In stator 7, stator grooves running in axial direction A are provided with windings 8, said windings 8 comprising a plurality of separately controllable windings 8a, 8b, 8c, 8d, 8e, and 8f, said windings further being controllable in such fashion that a magnetic rotary field can be produced. Windings 8, as shown in FIGS. 4h and 4i, can also be made in the form of three-phase drive winding WA with a pole pair number p and a three-phase coil winding WS with a pole pair number p+1 or p−1. A non-ferromagnetic housing 9 is located between stator 7 and axial impeller 2a. In the embodiment shown, magnetically active rotor part 1 with middle part 1c and parts 1f projecting starwise in the radial direction are provided. FIGS. 6d, 6e, 6f, and 6g show additional similar sections through magnetically effective rotor part 1 in different embodiments. In FIGS. 6d, 6e, 6f, 6g the axial path of blades 1b is not shown. Blades 1b according to FIGS. 6d, 6e, 6f, and 6g have a hydrodynamically effective path in axial direction A, with blades 1b having a corresponding twist.

Figure 6H:
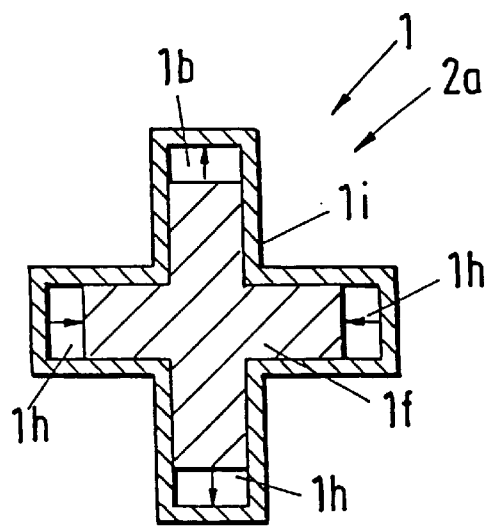

FIG. 6h shows a cross section through another embodiment of a magnetically effective rotor part 1 which likewise is in the form of an axial impeller 2a. Rotor part 1 comprises a body 1f with a cruciform shape, consisting of a ferromagnetic but not permanently magnetized metal, at whose tips permanent magnets 1h are provided. Body 1f as well as permanent magnets 1h are surrounded by a common jacket 1i, with jacket 1i consisting of a nonferromagnetic material such as a metal, titanium for example, or a plastic, especially a biocompatible plastic such as polycarbonate. This axial impeller 2a is drivable for example by a stator 7 according to the embodiment shown in FIG. 6c or FIG. 4a.

FIG. 8a shows a lengthwise section through a rotary pump 3 designed as a centrifugal pump 3b. Centrifugal pump 3b consists of a centrifugal pump part 99 that comprises housing 9 with internal centrifugal rotor 2b as well as well as a drive and bearing device indicated by teeth 7b, 7f of stator 7. Stator 7 can be designed as shown in the embodiment according to FIG. 1a or FIG. 4a. Housing 9 can be connected permanently or releasably with a drive device. In an advantageous embodiment of centrifugal pump 3b, housing 9, as shown in FIG. 8a, can be inserted partially between teeth 7b and 7f of stator 7 and rest loosely on the drive device. Housing 9 can thus be removed in simple fashion from stator 7 and replaced, for example. For example, when a centrifugal pump part 99 is used as a blood pump, centrifugal pump part 99 can be made as a disposable item. While centrifugal pump part 99 can be replaced after every use, the drive device can be used as often as desired to drive centrifugal impeller 2b located in centrifugal pump part 99. Centrifugal impeller 2b, as shown in FIGS. 1b, 1c, and 1d and described above, is suspended with zero contact by stator 7 and the magnetically acting forces as soon as centrifugal pump part 99 is located in the position provided in stator 7. By means of the passive and stabilizing and/or restoring forces acting to position rotor 2, the rotor can be mounted with zero contact relative to all six degrees of freedom in stator 7 or housing 9. It is important to keep in mind that the purely passively effected magnetic forces that influence the position of rotor part 1 in a stabilizing fashion, especially the force in axial direction z, are relatively small. In the event of higher forces engaging centrifugal impeller 2b in the z direction, the impeller would be raised relative to stator 7 or rotor 2 would strike housing 9 of centrifugal pump part 99. FIGS. 8a to 8h show various embodiments of centrifugal pump parts 99 which are also designed so that the forces acting in the z direction on rotor 2 are reduced in order to provide a bearing for rotor 2 with zero contact in housing 9 even while a fluid is being delivered.

Rotor 1 can be designed as an annular body in an embodiment according to FIGS. 2a, 2c, and 2e, or as a disc-shaped body according to an embodiment shown in FIGS. 10a, 10b; 11a, 11b; 13a, 13b. The embodiment according to FIG. 13a has a permanent magnet ir located between ferromagnetic material 1g. FIG. 9 shows a section through a rotor part 1 as well as adjacent stator teeth 7b and 7f, with the surfaces that are magnetically effective and face one another having groove-shaped recesses in order to apply an increased passively acting reluctance force in the opposite direction in the event of a deflection of rotor part 1 in axial direction A.

FIG. 8a shows a lengthwise section along line B—B through a centrifugal pump part 99 with a pump inlet opening 101 extending in the z direction. Centrifugal pump part 99 has a housing 9 with a rotor 2 located inside housing 9. Housing 9 is sealed liquid and gas-tight and has a pump opening 101 as well as a pump outlet opening 102 that extends radially with respect to rotor 2. Rotor 2 comprises an annular permanently magnetized rotor part 1 as shown in FIG. 2a, a rotor jacket 1a that surrounds rotor part 1, and a plurality of blades 1b uniformly distributed around the circumference of rotor 2, said blades forming an impeller.

The fluid entering in direction F1, in the vicinity of pump inlet opening 101, has a pressure p1. Adjacent to pump inlet opening 101 is a constriction 104 that acts as a nozzle, so that the fluid has a higher flow velocity after passing through the nozzle. The fluid is delivered into a downstream conducting means, not shown, through pump outlet 102 in direction F2 at pressure p3. In the graph in FIG. 8i, the pressure p of the fluid between housing 9 and annular body 1a is shown. This pressure produces a force acting in the z direction on rotor 2, which should be kept as low as possible. The force acting in the z direction is kept low in the embodiment according to FIG. 8a by rotor 2 being made in the form of an annular body, so that no force acting on rotor 2 in the z direction can be produced in the vicinity of the opening in the annular body. By virtue of this measure, during pump operation, only a small force develops that acts in the z direction on rotor 2. FIG. 8b shows a section through FIG. 8a along line A—A with housing 9, rotor 2b, annular body 1a and blades 1b and/or vanes 1b. Centrifugal rotor 2b is made annular.

FIG. 8c shows a lengthwise section and FIG. 8d shows a cross section through another embodiment of a centrifugal pump part 99. In addition to the design according to FIG. 8a, centrifugal rotor 2 has a circular impact plate 1k which is connected with annular body 1a by ribs 11 extending in the radial direction. Impact plate 1k is mounted perpendicularly to the direction of pump inlet opening 101 so that a significant part of the fluid flowing in direction F1, flowing in direction F3, strikes impact plate 1k and then breaks up into a plurality of partial streams F4. This impact plate 1k, especially at high delivery volumes of the fluid, produces a force on rotor 2 that acts in direction F1.

FIG. 8e shows a lengthwise section and FIG. 8f shows a cross section through another embodiment of the centrifugal pump part 99. In addition to the design according to FIG. 8a, centrifugal pump part 99 as shown has a tubular projection 105 in the shape of a hollow cylinder and extending in the axial direction and/or the z direction, said projection being mounted so that it abuts pump inlet opening 101. As a result, the fluid flowing in direction F1 is conducted directly into the center of annular body 1a. The length of tubular projection 105 can be made different. The static pressure of the fluid in the vicinity of the circular opening at the center of annular body 1a depends on the position of the outlet opening of tubular projection 105. Depending on the length of tubular projection 105, therefore, the force acting through the incoming fluid in F1-direction on rotor 2 can be determined. Thus, when centrifugal pump part 99 is filled with a fluid, no air bubbles form because tubular projection 105 has openings 105a so arranged that during the filling of a fluid through pump outlet opening 102, the fluid level rises inside housing 9 and any air bubbles that form in the interior of the rotor escape through openings 105 to pump inlet opening 101. FIG. 8f shows, in a sectional view along line D—D in FIG. 8e, annular rotor 2 with tubular projection 105 located in the center.

FIG. 8g shows a lengthwise section through another embodiment of a centrifugal pump part 99. Rotor 2, as described in detail in FIG. 8c, has an impact plate 1k connected by ribs 11 with annular body 1a. In addition, centrifugal pump part 99, as described in detail in FIG. 8e, has a tubular projection 105 in the form of a hollow cylinder. These two measures, during the delivery of the fluid, produce a force on rotor 2 that acts in flow direction F1. This force can be achieved by a plurality of additional measures with a corresponding design of the flow-determining components in order to influence the flow behavior of the fluid in such fashion that a force acting in the axial direction relative to rotor 2 is produced on said rotor. Thus for example, at the inside wall of housing 9, a projecting part 100a can be provided that extends over the entire circumference in order to reduce the pressure of the fluid between the bottom of housing 9 and rotor 2. FIG. 8h, in a detailed view, shows another measure for reducing this pressure, with a depression 100b extending over the entire circumference being provided on the bottom of housing 9 and annular body 1a having a projecting part 103f that is designed to match depression 110b and extends over the entire circumference. Sealing gap 103g between depression 10b in housing 9 and projecting part 103f in rotor 2 create a resistance to the fluid flowing around rotor 2. The flow resistance changes approximately proportionally to the width of sealing gap 103g. If the rotor is deflected upward, the flow resistance decreases, causing the pressure below the rotor to fall and the rotor to return to its original position. Thus, self-regulating rotor positioning in the axial direction is obtained.

The core idea, namely that the components of centrifugal pump part 99 that determine the flow of the fluid should be so designed that a force acting on centrifugal rotor 2b in the axial direction should be generated during the flow of the fluid, can be achieved by a plurality of hydrodynamic measures, so that the embodiments shown in FIGS. 8a to 8i represent only examples of a large number of possible embodiments.

FIG. 8k shows in schematic form and in a perspective view, a centrifugal pump 3b with centrifugal pump part 99 located in stator 7. Stator 7 in this embodiment is designed as a so-called temple motor, in which the flux irons 7y forming teeth 7a, 7b, 7c, 7d, 7e, 7f, 7g, and 7h are made L-shaped and coils 8a, 8b, 8c, 8d, 8e, 8f, 8g, and 8h are located in the portion of flux iron 7y that extends vertically. All teeth 7a, 7b, 7c, 7d, 7e, 7f, 7g, and 7h are coupled together magnetically by means of disk-shaped iron return 7z. The embodiments in FIGS. 1a and 8k can be controlled in an identical fashion and have the same effect on magnetically effective rotor part 1. One advantage of stator 7 on the embodiment shown in FIG. 8k consists in the fact that centrifugal pump part 99, made in the form of a replaceable part, can be inserted into and removed from stator 7 in an especially simple fashion. Teeth 7a, 7b, 7c, 7d, 7e, 7f, 7g, and 7h and the corresponding windings 8a, 8b, 8c, 8d, 8e, 8f, 8g, and 8h of stator 7 can be arranged in a wide variety of different ways, for example in an arrangement like that shown in FIGS. 4a, 4b, 4d, and 7, in which the magnetic return is always made through disk-shaped iron return 7z. The windings can be located in the horizontally or vertically extending sections of flux iron 7y.

The bearingless motor shown in FIG. 1a, comprising stator 7, rotor part im, and windings 8b, 8c, 8d, 8e, and 8f can also have a stator 7 according to the embodiment shown in FIG. 6c. The stator according to FIG. 6c has stator grooves extending in radial direction A with inserted windings 8. Teeth 7a, 7b, are located such that they pass between the stator grooves. If stator 7 according to FIG. 1a is replaced by stator 7 according to FIG. 6c, this stator 7 can have for example a drive winding WA as shown in FIG. 4h and a control winding WS as shown in FIG. 4i. FIG. 4h shows the winding diagram of drive winding WA which is inserted as a three-phase, two-pole, single-layer winding into stator 7 that has thirty-six grooves. FIG. 4i shows the winding diagram of control winding WS which is inserted as a three-phase, four-pole, single-layer winding into the thirty-six grooves of the same stator 7. Stator 7 of this kind with a rotor according to FIG. 1a can be driven by two three-phase a.c. power controllers, one each for drive winding WA and control winding WS. Rotor part 1, in stator 7 shown above, can also be designed as a cage rotor without being permanently magnetized or can have a short-circuited winding. To drive rotor part 1, a flow of current is induced in rotor part 1 by the rotary field generated in stator 7, so that a driving torque is exerted on rotor part 1 that is comparable to the driving principle of an induction motor.

FIG. 7 shows another embodiment of a stator 7 with twelve teeth extending in the radial direction and located around housing 9. Control winding WS consists of the four orthogonally mounted windings S1, S2, S3, and S4 while drive winding WA consists of windings A1, A2, A3, A4, A5, A6, A7, and A8. This stator 7 is suitable for driving a magnetically effective rotor part 1 according to an embodiment shown in FIGS. 2a to 2h or in FIGS. 10a, 10b, IIa, Iib, 13a, 13b, and for mounting it with zero contact. FIG. 7a shows an embodiment of a control device for stator 7 according to FIG. 7 for regulating the position of rotor 2 in the x direction. The current position xist of rotor 1 is determined by a position-measuring sensor 15 and this value is compared with a setpoint Xsoll, and the difference is supplied to a regulating device 20, which calculates an adjusting value Irx. Coil S1 as well as coil S2 are each powered through an amplifier 21 with a basic current Io. Adjusting value Irx is superimposed on basic current Io, with the sum being formed for the total current in coil S2 and the difference being formed for the total current in coil S4, so that a corresponding force acting in the x direction is exerted on rotor 2. FIG. 7b shows the same control device for regulating the position of rotor 2 in the y direction. The regulating difference ysoll minus yist is supplied to regulating device 20, which calculates an adjusting value Iry, said value being fed to coils S1 and S3 to produce a corresponding force acting in the y direction on rotor 2. FIG. 7c shows the control of coils A1, A2, A3, A4, A5, A6, A7, and A8 that produce the torque on rotor 2 or produce the magnetic rotary field. The coils are connected with two phases of a three-phase system, with the first phase generating a voltage sin (ωt) and the second phase generating a voltage sin (wt+120°), in other words, with a 120-degree phase shift relative to the first phase. Coils A4, A2, A8, and A6 are connected in series and are controlled by a common amplifier 21 with a first-phase voltage sin (ωt). Coils A3, A1, A7, and A5 are likewise connected in series and are controlled by a common amplifier 21 with a second-phase voltage sin (ωt+120°). By virtue of this control, a magnetic rotary field is generated in stator 7, said field generating a torque that acts in the circumferential direction on rotor 2 to drive said rotor.

FIG. 14a shows a lengthwise section through another embodiment of a centrifugal pump part 99 which, otherwise identically designed as the embodiment according to FIG. 8a, in addition has annularly designed permanent magnets 80a,80b,80c,80d for effecting a compensation of an axial thrust effective in the direction of axis A, whereby the rotor part 1 additionally comprises a cover plate 81 to which a permanent magnet 80c is fixedly attached. In the driving device comprising stator 7 with teeth 7a,7b,7c,7d,7e,7f,7g, 7h, there is additionally arranged an annular, axially polarized, permanent magnet 80a. Upon insertion of centrifugal pump part 99 into stator 7, housing 9 comes to lie above or on permanent magnet 80a. Rotor part 1 of centrifugal pump part 99 also has an annular permanent magnet 80b polarized in axial direction A, which is polarized in a direction opposite to that of permanent magnet 80a, so that a repulsive, permanently magnetically effected force occurs between permanent magnets 80a and 80b. Both permanent magnets 80a,80b are designed mutually adapted to one another with respect to their diameter such, that the magnetically effective front faces come to lie above each other, with centrifugal pump part 99 being inserted. Likewise, permantent magnet 80c, which is fixedly attached to rotor part 1 by means of cover plate 81 in the upper portion of rotor part 1, has a correspondingly adapted permanent magnet ring 80d, which is arranged outside centrifugal pump part 99 and which is resting on it. Both annular permanent magnets 80c,80d are polarized in opposite direction and, therefore, exert a repulsive, permanently magentically effected force on one another. In an advantageous embodiment permanent magnets 80b,80c , which are arranged inside centrifugal pump part 99, are designed smaller or susbstantially smaller than permanent magnets 80a and 80d located outside. This arrangement is especially advantageous if centrifugal pump part 99 is designed as a single use article, e.g. as a blood pump, which is destroyed after single use.

FIG. 14b shows a lengthwise section through another embodiment of an axial pump 3a which, otherwise identically designed as the embodiment according to FIG. 5a, in addition has annularly designed permanent magnets 80a, 80b,80c,80d,80e,80f for effecting an axial thrust compensation effective in the direction of axis A. At both sides of rotor 2 at the end portion thereof, there is cast integral an annular permanent magnet 80b,80c , which is polarized in axial direction A. In the fixedly arranged housing 9 additional annular permanent magnets 80a,80d,80e,80f are arranged and polarized such, that a permanently magnetically effected, repulsive force is generated upon rotor 2 in axial direction A at both sides. By this arrangement of the permanent magnets 80a,80b,80c,80d,80e,80f, a thrust compensation effective in axial direction A is effected. In both embodiments represented in FIG. 14a and FIG. 14b, there is a plurality of meaningful possibilities of arrangements of the permanent magnets 80a,80b,80c,80d,80e,80f for generating an axial thrust compensation effected by permanent magnetic forces. For example, axial pump 3a may only have the left-handedly arranged permanent magnets 80a,80b in order to generate a thrust compensation effective in axial direction A. Also, the arrangement according to FIG. 14a could only have the permanent magnets 80a,80b arranged in the lower portion in order to generate a thrust compensation effective in axial direction. The annularly extending permanent magnets 80a,80b,80c,80d,80e,80f may, for example, be composed of a plurality of single segments. Permanent magnets 80a,80b,80c,80d,80e,80f may also be radially polarized and, advantageously, be arranged slightly shifted and above each other in order to generate a permanently magnetically generated force effective in axial direction. Certain permanent magnets 80,80b may also be radially magnetized while the remaining permanent magnets 80c,80d,80e,80f are axially polarized, whereby the permanent magnets are arranged mutually effective to one another such, that a force effective in axial direction is generated.

We claim:

1. A rotary pump having a bearingless motor and comprising in combination:
   a housing defining an inlet, an outlet, and a passage extending between the inlet and the outlet for enabling a fluid to be pumped from the inlet, through the passage, and out the outlet;
   a stator arranged to extend around the housing defining the passage, said stator having a plurality of magnetically conducting teeth wound with electrical windings;
   a rotor with fluid impelling blades contained inside the housing at the passage for rotating within the passage around an axis and causing fluid to be pumped from the inlet to the outlet of the housing;
   said rotor comprising a passive magnetically effective rotor part;
   a control to the electrical windings generating a rotating magnetic field for rotation of the rotor and a controllable magnetic field for positioning of the passive magnetically effective rotor part relative to the stator in a plane normal to the axis;
   the passive magnetically effective rotor part having passive magnetic attraction to the magnetically conducting teeth of the stator to resist rotor displacement along the axis and tilting relative to a plane normal to the axis.

2. A rotary pump having a bearingless motor according to claim 1 and comprising in further combination:
   the passive magnetically effective rotor part having a diameter dimension normal to the axis which is at least twice as great as a thickness dimension parallel to the axis.

3. A rotary pump having a bearingless motor according to claim 1 and comprising in further combination:
   the passive magnetically effective rotor part is disc shaped.

4. A rotary pump having a bearingless motor according to claim 1 and comprising in further combination:
   the passive magnetically effective rotor part is annular.

5. A rotary pump having a bearingless motor according to claim 1 and comprising in further combination:
   the passive magnetically effective rotor part is a star shaped body.

6. A rotary pump having a bearingless motor according to claim 1 and comprising in further combination:
   the passive magnetically effective rotor part is a cage rotor.

7. A rotary pump having a bearingless motor according to claim 1 and comprising in further combination:
   the rotor with fluid impelling blades is surround by a jacket of non-ferromagnetic material selected from the group consisting of plastic, non-ferromagnetic metal, ceramic and biocompatible material.

8. A rotary pump having a bearingless motor according to claim 1 and comprising in further combination:
   the active electrical control to the electrical windings generating a rotating magnetic field within the plurality of magnetically conducting teeth for rotation of the rotor is selected from the group consisting of a reluctance motor drive, a synchronous motor drive and an induction rotor drive.

9. A rotary pump having a bearingless motor according to claim 1 and comprising in further combination:
   the stator has a drive winding with a number of pole pairs P and control windings with pole pair numbers P+1 or P−1.

10. A rotary pump having a bearingless motor according to claim 1 and comprising in further combination:
    an emergency bearing provided in the housing for engagement of the rotor in an emergency.

11. A rotary pump having a bearingless motor according to claim 1 and comprising in further combination:
    the housing and the rotor defining a passage for forming a hydrodynamic bearing for effecting a hydraulic force on the rotor.

12. A rotary pump having a bearingless motor according to claim 1 and comprising in further combination:
    the rotor defines a central recess; and,
    the central recess including impelling vanes arranged in the central recess.

13. A rotary pump having a bearingless motor according to claim 1 and comprising in further combination:
    the rotor has protruding axial blades.

14. A rotary pump having a bearingless motor according to claim 1 and comprising in further combination:
    the rotary pump is an axial pump.

15. A rotary pump having a bearingless motor according to claim 1 and comprising in further combination:
    the rotary pump is a centrifugal pump.

16. A rotary pump having a bearingless motor according to claim 15 and comprising in further combination:
    flow inducing partial elements are affixed to the rotor to exert a force on the rotor of the centrifugal pump.

17. A rotary pump having a bearingless motor according to claim 1 and comprising in further combination:
    the rotor defines a pump inlet co-axial to the inlet of the housing and impelling vanes from the pump inlet into the housing; and,
    the housing defines the pump outlet peripherally of the rotor.

18. A rotary pump having a bearingless motor according to claim 1 and comprising in further combination:
    sensors are located proximate the teeth for detection of the position of the rotor relative to the housing; and,
    the sensors are operatively connected to the actively controllable magnetic field for positioning of the passive magnetically effective rotor part relative to the stator.

19. A method of controlling a rotary pump having a bearingless motor comprising the steps of:

provSiding a housing defining an inlet, an outlet, and a passage extending between the inlet and the outlet for enabling a fluid to be pumped from the inlet, through the passage, and out the outlet;

providing a stator arranged to extend around the housing defining the passage, said stator having a plurality of magnetically conducting teeth wound with electrical windings;

providing a rotor with fluid impelling blades contained inside the housing at the passage for rotating within the passage around an axis and causing fluid to be pumped from the inlet to the outlet of the housing;

said rotor having a passive magnetically effective rotor part;

controlling the electrical windings to generate a rotating magnetic field for rotation of the rotor; and controlling the electrical windings to generate a magnetic field in the windings for positioning of the passive magnetically effective rotor part relative to the stator in a plane normal to the axis; and, providing the passive magnetically effective rotor part with passive magnetic attraction to the magnetically conducting teeth of the stator to resist rotor displacement along the axis and tilt relative to a plane normal to the axis.

* * * * *